(12) United States Patent
Puppala et al.

(10) Patent No.: US 9,822,504 B2
(45) Date of Patent: Nov. 21, 2017

(54) SYSTEMS, APPARATUSES AND METHODS FOR ASSESSING SOIL HEAVE

(71) Applicants: Board of Regents, The University of Texas System, Austin, TX (US); Case Western Reserve University, Cleveland, OH (US)

(72) Inventors: Anand Puppala, Southlake, TX (US); Xiong Yu, Beachwood, OH (US)

(73) Assignee: Board of Regents, The University of Texas System, Austin, TX (US)

(*) Notice: Subject to any disclaimer, the term of this patent is extended or adjusted under 35 U.S.C. 154(b) by 292 days.

(21) Appl. No.: 14/595,189

(22) Filed: Jan. 12, 2015

(65) Prior Publication Data

US 2015/0197908 A1 Jul. 16, 2015

Related U.S. Application Data

(60) Provisional application No. 61/926,174, filed on Jan. 10, 2014.

(51) Int. Cl.
*G01N 3/00* (2006.01)
*G01M 7/00* (2006.01)
*E02D 1/02* (2006.01)
*G01N 27/04* (2006.01)
*G01N 33/24* (2006.01)

(52) U.S. Cl.
CPC ........... *E02D 1/022* (2013.01); *G01N 27/048* (2013.01); *G01N 33/24* (2013.01)

(58) Field of Classification Search
CPC ....... E02D 1/022; G01N 33/24; G01N 27/048
USPC ..................................... 324/696; 73/84, 594
See application file for complete search history.

(56) References Cited

U.S. PATENT DOCUMENTS

| 7,082,831 B2* | 8/2006 | Xiangwu ................ E02D 1/022 73/594 |
| 7,581,446 B2 | 9/2009 | Troxler |
| 2003/0014923 A1 | 1/2003 | Robbins |
| 2005/0252295 A1 | 11/2005 | Fink et al. |
| 2006/0257210 A1 | 11/2006 | Williams |
| 2008/0304919 A1 | 12/2008 | Coyle |
| 2009/0314090 A1 | 12/2009 | Troxler |

(Continued)

OTHER PUBLICATIONS

Kenichi Soga, "Lecture 3 : Time Effects Observed in Granular Materials," Feb. 2005, 22 unnumbered pages, available at http://www.eng.hokudai.ac.jp/COE-area/workshop/pdf/05feb_lec_soga3.pdf.

*Primary Examiner* — Farhana Hoque
(74) *Attorney, Agent, or Firm* — Hirsch & Westheimer, PC

(57) ABSTRACT

A method of assessing soil heave includes providing a plurality of determined values of a shear modulus of soil, the determined values being values of the shear modulus of the soil at different times; and determining a change over time in the shear modulus of the soil, based on the plurality of determined values of the shear modulus of the soil. The soil may have been treated by adding a stabilizer to the soil. The soil may be hydrated. A system for assessing soil heave includes a bender element disposed in soil, for determining a change over time of a shear modulus of the soil, and a time domain reflectometer probe disposed in the soil, for determining a change over time of moisture content of the soil. The determined change over time of the shear modulus and the determined change over time of the moisture content are used to assess heaving of the soil.

16 Claims, 7 Drawing Sheets

(56) References Cited

U.S. PATENT DOCUMENTS

2011/0033247 A1    2/2011   Deng et al.
2012/0056627 A1    3/2012   Troxler
2012/0269035 A1   10/2012   Foley \* cited by examiner

SYSTEMS, APPARATUSES AND METHODS FOR ASSESSING SOIL HEAVE

CROSS-REFERENCE TO RELATED APPLICATIONS

This application claims the benefit of the filing date of U.S. Provisional Patent Application No. 61/926,174, filed on Jan. 10, 2014, by the inventors of this application, and incorporated herein by reference.

STATEMENT REGARDING FEDERALLY SPONSORED RESEARCH

This invention is based in part upon work supported by the National Academy of Sciences under Grant No: NCHRP-154.

FIELD OF THE INVENTION

This disclosure relates generally to systems, apparatuses and methods for assessing soil heave, and more particularly to the case of sulfate-induced heaving in stabilized soils.

BACKGROUND

Expansive soils, also known as shrink-swell soils, are soils that exhibit large changes in volume, i.e., that swell and shrink, due to various factors, including moisture content, type and amount of clay minerals, dry density, soil structure, confining pressure and climatic conditions. Both the swelling and the shrinkage of expansive soils can cause severe damage to civil engineering structures, such as pavement structures (e.g., roads, runways, etc.), buildings, embankments, etc. This damage is understood to incur billions of dollars of structural repair and reconstruction work in the U.S. annually.

Effective and efficient methods, apparatuses, and systems for assessing soil for the potential of expansion would be desirable, so that pre-emptive measures for mitigating this problem could be taken with respect to the soil prior to building structures thereon.

SUMMARY OF THE INVENTION

Embodiments of the present invention provides systems, apparatuses, and methods that may be used to assess soil heave.

According to a first aspect of the invention, there is provided a method that may be used to assess soil heave. The method includes providing a plurality of determined values of a shear modulus of soil, the determined values being values of the shear modulus of the soil at different times; and determining a change over time in the shear modulus of the soil, based on the plurality of determined values of the shear modulus of the soil.

According to a second aspect of the invention, there is provided a system that may be used to assess soil heave. The system includes a bender element disposed in soil, for determining a change over time of a shear modulus of the soil, and a time domain reflectometer probe disposed in the soil, for determining a change over time of moisture content of the soil. The determined change over time of the shear modulus and the determined change over time of the moisture content are used to assess heaving of the soil.

Other systems, apparatuses, methods, and articles of manufacture are also provided.

BRIEF DESCRIPTION OF THE DRAWINGS

The following figures form part of the present specification and are included to further demonstrate certain aspects of the present claimed subject matter, and should not be used to limit or define the present claimed subject matter. The present claimed subject matter may be better understood by reference to one or more of these drawings in combination with the description of embodiments presented herein. Consequently, a more complete understanding of the present embodiments and further features and advantages thereof may be acquired by referring to the following description taken in conjunction with the accompanying drawings, in which like reference numerals may identify like elements, wherein:

DETAILED DESCRIPTION OF DISCLOSED EMBODIMENTS

Figure 1:
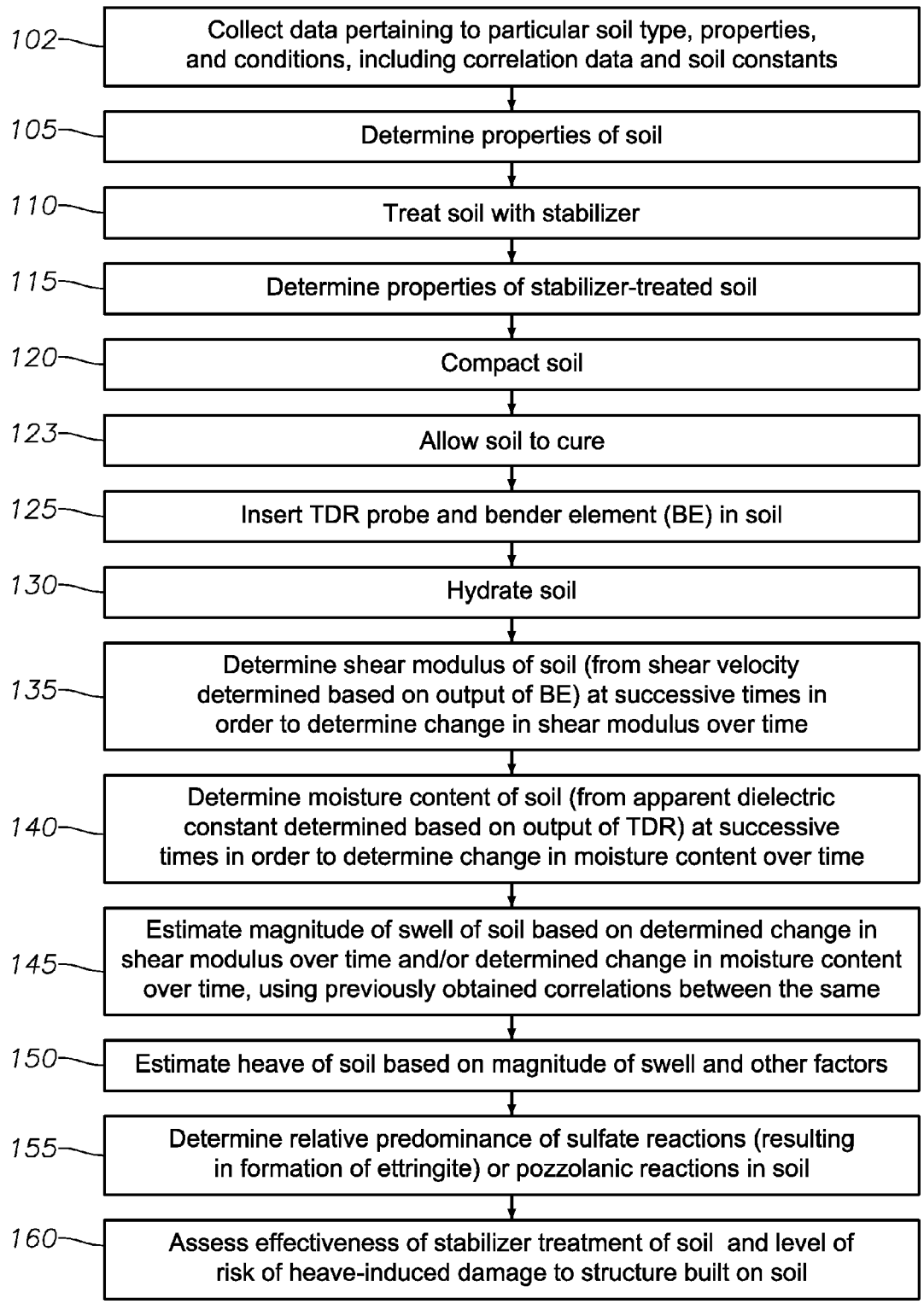
FIG. 1 is a flow chart illustrating a method for assessing soil heave, according to some embodiments.

While various embodiments are described herein, it should be appreciated that the present invention encompasses many inventive concepts that may be embodied in a wide variety of contexts. Thus, the following detailed description of exemplary embodiments, read in conjunction with the accompanying drawings, is merely illustrative and is not to be taken as limiting the scope of the invention. Rather, the scope of the invention is defined by the appended claims and equivalents thereof.

Illustrative embodiments of the invention are described below. In the interest of clarity, not all features of an actual implementation are necessarily described for each embodiment disclosed in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Chemical stabilization is a common technique for mitigating the problem of swelling and shrinking of expansive soils. In this technique, a stabilizer, such as lime, cement or another calcium-based stabilizer, is added to the expansive soil to reduce the degree of swelling and shrinking, and increase the strength, of the expansive soil. The calcium-based stabilizer takes effect by means of chemical reactions called pozzolanic reactions. In these reactions, the calcium compounds in the stabilizer react with compounds in the soil, in the presence of water, to produce compounds possessing cementitious properties, i.e., compounds that, like cement, can set and harden, binding other materials together.

However, it has been found that in the case of soil that contains a significant level of sulfates ("sulfate soils"), calcium-based stabilization may not be successful and may in fact weaken the soil and exacerbate the problem of soil expansion. Sulfates may occur naturally in soil (e.g., gypsum) but are also added to soil from industrial waste (e.g., phosphogypsum), which is sometimes used as base and subbase material to support pavements. The reason for the observed failure of calcium-based stabilization in sulfate soils is understood to be that the sulfate minerals react with the calcium component of the stabilizer and free reactive alumina of the soil, in the presence of water, to form highly expansive crystalline minerals, namely, ettringite and thaumasite. In this disclosure, these reactions will be referred to as "sulfate reactions." In this context, ettringite is the predominant mineral formed, and thaumasite is formed from ettringite at certain low temperature conditions. Both ettringite and thaumasite may continue to expand, e.g., in the presence of water and under certain conditions of temperature and humidity. The formation and growth of these minerals thus results directly in expansion or swelling of the soil. The expansion or swelling due to ettringite and thaumasite is referred to as "sulfate-induced heave." "Heave" refers to the upward movement of soil, and is thus correlated with the expansion or swelling of soil. In the case of sulfate-induced heave, the magnitude of heave is a function primarily of the quantity of ettringite formed, the crystal morphology and size of the ettringite formation, the restraint of the soil system, and the level of ion accessibility in the soil. These factors in turn depend on soil type and properties (e.g., degree of compaction, void ratio) and various environmental conditions, including pH conditions, temperature, and the presence of soluble sulfates, carbonates and water. The time required for sulfate-induced heave to occur after treatment of soil with calcium-based stabilizers varies widely, over a range extending at least from as short as a few days to as long as eighteen months. This variation is due to variation in, e.g., soil properties and environmental conditions.

It will also be noted that ettringite and thaumasite, at least in hydrated form, are soft, jell-like minerals, so that their presences softens the soil. Thus, the presence of ettringite and thaumasite in the soil may weaken the soil due to both their expansive and their softening properties.

While it is thus understood that significant levels of sulfates in the soil may render calcium-based stabilization ineffective, researchers have been unable to conclusively establish threshold levels of sulfates that lead to sulfate-induced heave. This failure to conclusively establish such threshold levels is attributed primarily to the variability of soil types and of the site conditions at which the various studies have been carried out.

As will be understood from the above discussion, when a calcium-based stabilizer is added to soil, both the desired, strengthening and stabilizing, pozzolanic reactions and the undesired, weakening and destabilizing, sulfate reactions may occur. Where the 'good' pozzolanic reactions predominate, the magnitude of sulfate-induced heave will be low or none and the stabilization treatment may be deemed successful; where the 'bad' sulfate reactions predominate, the magnitude of sulfate-induced heave will be significant or high and the stabilization treatment may be deemed unsuccessful. As there are no definitive threshold levels of sulfates that lead to sulfate-induced heave, it is not known from the amount of sulfates in soil whether the 'good' pozzolanic reactions or the 'bad' sulfate reactions will predominate upon stabilization treatment.

In view of the above, it will be understood that the potential of sulfate-induced heave, e.g., the expected magnitude and timeframe thereof (time required for heave to occur), varies widely over different soils and different sites, because it is dependent on a large number of factors (e.g., soil properties, environmental conditions), which themselves generally may vary over a wide range of values. To minimize the likelihood of damage to structures due to heaving, it would be useful to be able to assess a given soil/site for the potential of heaving (e.g., predict the magnitude and timeframe of heaving) in advance of building on it. However, at least because the timeframe may vary so widely, current tests (conducted in the laboratory) for assessing heave may take weeks or months to complete. In the practical reality of the construction industries involved in building homes, roads, etc., it is generally not feasible to delay construction for the length of time necessary to obtain results of such tests.

Accordingly, a quicker test for assessing heave would be useful, and the instant inventors have developed such tests. These tests also determine the relative predominance of pozzolanic reactions or sulfate reactions in soil, assesses the effectiveness of the application of calcium-based stabilizers to the soil (which may also be referred to as the treatment of the soil with calcium-based stabilizers), and assess the risk of heave-induced damage to structures that would be constructed on the soil.

One aspect of the development of the inventors' tests for assessing heave was the collection of data for use in the tests. Using soil samples in the laboratory, data was collected correlating swell of the soil with shear modulus, moisture content, and dry density, or their change over time. Such correlation data was collected for a variety of soils of different types and properties (e.g., different soil classifications, different Atterberg limits, different sulfate levels, etc.) and under different conditions (e.g., type and dosage of stabilizer added). (Accordingly, data was also collected to ascertain soil properties of the various soil types.) The collected correlation data is used in carrying out the heave assessment tests on soil in the field. Where it is desired to carry out heave assessment tests on soil of types and properties (or under conditions) other than those for which data has been collected, additional data for such soil types, properties and conditions may be collected for use in carrying out the tests for such soil types, properties and conditions.

Examples of data collection are now described. Data was collected on three different soils, at different sulfate levels, at different moisture contents, with different stabilizers and at different stabilizer dosages. The three soils are referred to as Burleson, Okla. and Riverside soils. Atterberg limit tests were conducted on all three soils as per ASTM D-4318 to determine the liquid limit, plastic limit and plasticity index of the soils. The results of the Atterberg limit tests are summarized in Table 1 below. Also, as indicated in Table 1, the Burleson, Okla. and Riverside soils are classified as high plasticity clay (CH), low plasticity clay (CL), and low plasticity clay (CL), respectively, according to the Unified Soil Classification System (USCS) classification system. The three soils have different geological origins.

Sulfate contents of the three soils were determined. Soils with lower sulfate contents (Burleson and Riverside soils) were spiked with highly soluble sodium sulfate ($Na_2SO_4$) to bring their sulfate contents to 12,000 ppm and 20,000 ppm, respectively. The initial and elevated (spiked) soluble sulfate contents of the three soils are presented in Table 2 below. Based on their elevated sulfate contents, the three soils were classified as low (Burleson), medium (Oklahoma) and high (Riverside) sulfate soils.

TABLE 1

Atterberg Limits and Soil Classification

| Soil | Atterberg Limits | | | USCS Classification |
|---|---|---|---|---|
| | Liquid Limit | Plastic Limit | Plasticity Index | |
| Burleson | 55 | 18 | 37 | CH |
| Oklahoma | 35 | 11 | 24 | CL |
| Riverside | 42 | 21 | 21 | CL |

TABLE 2

Sulfate Contents of the Test Soils

| Soil Location | Initial Sulfate Contents, ppm | Elevated Sulfate Contents, ppm |
|---|---|---|
| Burleson | 1,900 | 12,000 |
| Oklahoma | 15,000 | 15,000 |
| Riverside | 500 | 20,000 |

The different compaction moisture contents used were optimum moisture content (OMC), corresponding to maximum dry density (MDD) and wet of optimum moisture content (WOMC), corresponding to 95% maximum dry density. The stabilizers used were lime and cement, and the dosages used were 4% and 8% for lime and 3% and 6% for cement. The dosages were based on the dry weight of the test soils. These testing variables are summarized in Table 3 below.

TABLE 3

Testing Variables

| Description | Variables |
|---|---|
| Soils | Three (Burleson, Oklahoma and Riverside) |
| Sulfate Contents | Three (12,000 ppm, 15,000 ppm and 20,000 ppm) |
| Moisture Contents | Two (Optimum and Wet of Optimum Moisture Contents) |
| Stabilizers | Cement and Lime |
| Stabilizer Dosages | 3% and 6% (Cement) & 4% and 8% (Lime) |

In order to determine the compaction moisture content and dry unit weight relationships of the soils, standard Proctor compaction tests were conducted on samples of the three soils to establish compaction relationships. The ASTM-D 698 procedure was followed to determine the compaction curves and then establish maximum dry density and corresponding optimum moisture content. The soil samples were treated with lime and cement at the respective dosages, and Proctor curves were established for the treated soils. Compaction test results on natural and treated soils are summarized in Tables 4-8 below.

TABLE 4

Summary of Standard Proctor Test Results on Untreated Soils

| Soil | Sulfate Content, Ppm | Moisture Content (%) | | Maximum Dry Density ($lb/ft^3$) | |
|---|---|---|---|---|---|
| | | OMC | WOMC | OMC | WOMC |
| Burleson | 12,000 | 20 | 24.8 | 99.2 | 94.24 |
| Oklahoma | 15,000 | 18 | 22.4 | 104 | 98.8 |
| Riverside | 20,000 | 16 | 20.2 | 106.4 | 101.08 |

TABLE 5

Summary of Standard Proctor Test Results on 3% Cement-Treated Soils

| Soil | Sulfate Content, Ppm | Moisture Content (%) | | Maximum Dry Density ($lb/ft^3$) | |
|---|---|---|---|---|---|
| | | OMC | WOMC | OMC | WOMC |
| Burleson | 12,000 | 19.6 | 21.8 | 104.8 | 99.6 |
| Oklahoma | 15,000 | 17.8 | 19.8 | 106.8 | 101.6 |
| Riverside | 20,000 | 15.6 | 17.8 | 99.8 | 94.8 |

TABLE 6

Summary of Standard Proctor Test Results on 6% Cement-Treated Soils

| Soil | Sulfate Content, Ppm | Moisture Content (%) | | Maximum Dry Density ($lb/ft^3$) | |
|---|---|---|---|---|---|
| | | OMC | WOMC | OMC | WOMC |
| Burleson | 12,000 | 19.4 | 21.5 | 105.2 | 99.9 |
| Oklahoma | 15,000 | 17.6 | 19.6 | 108 | 102.6 |
| Riverside | 20,000 | 15.3 | 17.5 | 100.4 | 95.4 |

TABLE 7

Summary of Standard Proctor Test Results on 4% Lime-Treated Soils

| Soil | Sulfate Content, Ppm | Moisture Content (%) | | Maximum Dry Density ($lb/ft^3$) | |
|---|---|---|---|---|---|
| | | OMC | WOMC | OMC | WOMC |
| Burleson | 12,000 | 20.8 | 25.7 | 103.2 | 98.0 |
| Oklahoma | 15,000 | 20.4 | 24 | 99.6 | 94.6 |
| Riverside | 20,000 | 19 | 23.6 | 98.8 | 93.8 |

TABLE 8

Summary of Standard Proctor Test Results on 8% Lime-Treated Soils

| Soil | Sulfate Content, Ppm | Moisture Content (%) | | Maximum Dry Density (lb/ft³) | |
|---|---|---|---|---|---|
| | | OMC | WOMC | OMC | WOMC |
| Burleson | 12,000 | 22 | 26.2 | 102.5 | 97.4 |
| Oklahoma | 15,000 | 21 | 24.6 | 98 | 93.1 |
| Riverside | 20,000 | 20 | 25.1 | 98.4 | 93.5 |

Before conducting the shear modulus measurements, the maximum possible volumetric (three-dimensional) swell strain was measured. Though the laboratory swell tests do not give vertical and horizontal swell strains in the field situation, they provide the maximum amount of swelling that is possible in "ideal" conditions. These swell strains are used to correlate the strength or stiffness property changes due to the sulfate reactions. Thus, any stiffness or small strain shear modulus property changes is understood to indirectly account for the heave phenomenon observed in the treated sulfate soils.

To determine the maximum volumetric swell potential, a three-dimensional free swell test was conducted. Three dimensional volumetric swell strain tests were conducted using the so-called double inundation technique to determine the maximum possible radial and vertical swell strain of a large soil specimen. Double inundation represents the worst possible scenario in a field where 100% saturation of the soil can be achieved after a continuous rainfall event. Thus, maximum expansive heave can be achieved in a short testing period in the laboratory environment. Oven-dried soils were pulverized and mixed with stabilizers at targeted moisture content levels. Both control and treated soil specimens were mixed and then compacted using a Gyratory Compactor Machine at two pre-established compaction moisture content levels.

For the volumetric swell tests, the samples were 4 inches (101.6 mm) in diameter and 4.6 inches (116.8 mm) in height and were covered by a rubber membrane. Porous stones were placed on both top and bottom of the soil specimens, which facilitated the movement of water to the soil specimen. The specimen was fully soaked under water in a large container. As noted, swell tests were performed on chemically-treated sulfate soils under moisture inundation from both ends of the soil specimen. As noted, the presence of moisture facilitates the sulfate reactions in the sulfate soils that result in ettringite crystal formation. Hence, swell tests were performed under full soaking conditions. The amount of soil heave in both vertical and diametrical directions was continuously monitored until there was no significant swell for 24 hours.

At the end of the monitoring period, radial measurements were taken at the top, middle, and bottom circumferences of the soil samples and averaged at a frequency similar to the Consolidation Test. The percent vertical and radial strain values are calculated based on the original dimensions of the soil specimen and these strains are used in the estimation of total volumetric strains. Tables 9 and 10 show the volumetric swell of cement-treated and lime-treated soils, respectively, with comparison to the untreated soils. Tables 11-15 show the vertical, radial and volumetric swell strains of natural and treated soils (3% cement, 6% cement, 4% lime and 8% lime), respectively. Although not shown in the tables, curves of vertical swell strain versus elapsed time for all the natural and treated soils at optimum moisture content show a steep increase in strain during a very short initial period of time (as little as a few to several hours), followed by a gradual tapering off of the increase in strain over a relatively long period of time (around 160 hours).

TABLE 9

Volumetric Swell Strains of Natural and Cement-Treated Soils

| Soil | Sulfate Content, ppm | Natural | | 3% Cement | | 6% Cement | |
|---|---|---|---|---|---|---|---|
| | | OMC | WOMC | OMC | WOMC | OMC | WOMC |
| Burleson | 12,000 | 10.9 | 5.2 | 12.8 | 10.3 | 16.1 | 11.3 |
| Oklahoma | 15,000 | 8.4 | 5 | 11.2 | 9.8 | 14.3 | 10.5 |
| Riverside | 20,000 | 10.2 | 10 | 13.8 | 10.4 | 15.2 | 11 |

TABLE 10

Volumetric Swell Strains of Natural and Lime-Treated Soils

| Soil | Sulfate Content, ppm | Natural | | 4% Lime | | 8% Lime | |
|---|---|---|---|---|---|---|---|
| | | OMC | WOMC | OMC | WOMC | OMC | WOMC |
| Burleson | 12,000 | 10.9 | 5.2 | 17.2 | 13.1 | 15.6 | 10.8 |
| Oklahoma | 15,000 | 8.4 | 5 | 10.8 | 8.4 | 14.6 | 11 |
| Riverside | 20,000 | 10.2 | 10 | 14.8 | 11.6 | 16 | 12.7 |

As seen from Tables 9 and 10, the swell strain values of both lime-treated and cement-treated soils are significantly higher than the same of the control (natural) soils, and this increase is attributed to the deleterious sulfate reactions that occurred in the treated soils. The same soils were further monitored for stiffness and moisture variations using an embedded bender element and TDR probe.

TABLE 11

Vertical, Radial and Volumetric Swell Strains (Natural)

| | Natural Soil | | | | | |
|---|---|---|---|---|---|---|
| | Vertical Strain (%) | | Radial Strain (%) | | Volumetric Strain (%) | |
| Soil Type | OMC | WOMC | OMC | WOMC | OMC | WOMC |
| Burleson | 5.2 | 3.2 | 2.75 | 1.0 | 10.9 | 5.2 |
| Oklahoma | 4.2 | 2.6 | 2.1 | 1.2 | 8.4 | 5 |
| Riverside | 4.8 | 4.0 | 2.7 | 3.0 | 10.2 | 10 |

TABLE 12

Vertical, Radial and Volumetric Swell Strains (3% Cement)

| | 3% Cement | | | | | |
|---|---|---|---|---|---|---|
| | Vertical Strain (%) | | Radial Strain (%) | | Volumetric Strain (%) | |
| Soil Type | OMC | WOMC | OMC | WOMC | OMC | WOMC |
| Burleson | 6.6 | 5.0 | 3.1 | 2.65 | 12.8 | 10.3 |
| Oklahoma | 6.2 | 5.2 | 2.5 | 2.3 | 11.2 | 9.8 |
| Riverside | 7.3 | 5.2 | 3.25 | 2.6 | 13.8 | 10.4 |

TABLE 13

Vertical, Radial and Volumetric Swell Strains (6% Cement)

| | 6% Cement | | | | | |
|---|---|---|---|---|---|---|
| | Vertical Strain (%) | | Radial Strain (%) | | Volumetric Strain (%) | |
| Soil Type | OMC | WOMC | OMC | WOMC | OMC | WOMC |
| Burleson | 7.6 | 6.0 | 4.25 | 2.65 | 16.1 | 11.3 |
| Oklahoma | 7.4 | 5.8 | 3.45 | 2.35 | 14.3 | 10.5 |
| Riverside | 8.2 | 6.0 | 3.5 | 2.5 | 15.2 | 11 |

TABLE 14

Vertical, Radial and Volumetric Swell Strains (4% Lime)

| | 4% Lime | | | | | |
|---|---|---|---|---|---|---|
| | Vertical Strain (%) | | Radial Strain (%) | | Volumetric Strain (%) | |
| Soil Type | OMC | WOMC | OMC | WOMC | OMC | WOMC |
| Burleson | 8.2 | 6.1 | 4.5 | 3.5 | 17.2 | 13.1 |
| Oklahoma | 6.2 | 4.4 | 2.3 | 2.0 | 10.8 | 8.4 |
| Riverside | 5.8 | 4.2 | 4.5 | 3.8 | 14.8 | 11.6 |

TABLE 15

Vertical, Radial and Volumetric Swell Strains (8% Lime)

| | 8% Lime | | | | | |
|---|---|---|---|---|---|---|
| | Vertical Strain (%) | | Radial Strain (%) | | Volumetric Strain (%) | |
| Soil Type | OMC | WOMC | OMC | WOMC | OMC | WOMC |
| Burleson | 8.0 | 5.6 | 3.8 | 2.6 | 15.6 | 10.8 |
| Oklahoma | 6.5 | 5.2 | 4.05 | 2.9 | 14.6 | 11 |
| Riverside | 7.2 | 4.9 | 4.4 | 3.9 | 16 | 12.7 |

Small stain shear modulus (stiffness) measurements were also made as part of the task of developing a database of moisture content, dry density and moduli properties of chemically treated sulfate soils that are close to or far from problematic heaving conditions. This data is analyzed in developing criteria for algorithms to be used with the bender element and TDR sensors for field and laboratory testing conditions. The bender element sensor was used to monitor moisture content, dry unit weight and stiffness property variations. All three soils were used.

Natural and treated soil samples were prepared at two moisture conditions: OMC and WOMC (95% of maximum dry density). A bender element was embedded in both the natural and treated specimens. Treated specimens were cured at room temperature and soaked for swell testing. The samples were soaked for a period until the degree of saturation reached unity. Sample saturation time varied from one day for untreated soils to three days for cement-treated and lime-treated samples. Once the sample was fully saturated, soil moisture, stiffness and density changes were monitored continuously. In addition to this, simultaneous volume changes were measured (described above).

Stiffness measurements were made on the natural and treated soil samples using the embedded bender element. As described above, while cement and lime treatment are known to improve the moduli properties of soils, in the case of soils having high sulfate levels the strength enhancements due to lime and cement treatment have been found to be minimal, and in some cases strength reductions have been observed. Also, strength enhancements have been found to be smaller in samples cured by soaking compared to those cured in a humidity room. In the tests described in this disclosure, samples were cured by submerging them in water.

For comparison purposes, Riverside soil, in its natural condition (500 ppm sulfate contents), was also treated with both stabilizers (lime and cement), and small strain shear modulus measurements on these treated soils were taken. The reason for choosing the Riverside soil for this investigation is that it has a natural low sulfate content (500 ppm), which is not considered problematic for lime and cement treatments. In Riverside soil, shear modulus enhancements of up to 50% were observed with lime and cement treatment, indicating no ettringite reactions were taking place in these low sulfate soils.

For the high sulfate soils considered in the current study, it was observed that small strain shear modulus decreased with an elapsed time period in both lime-treated and cement-treated soils. This could be attributed to the formation of ettringite and subsequent expansion leading to the softening of the treated soil. Higher shear moduli values were observed in cement-treated soils compared to the lime-treated soils. This could be attributed to the early pozzolanic reactions occurring with the cement treatment. Though the shear moduli of cement-treated soils were higher, the percent loss of moduli was greater in the case of cement-treated soils as compared to lime-treated soils.

Soaked soil samples with the bender element were weighed before stiffness measurements. It has been reported in the literature that ettringite formation and its crystal growth enhances the moisture retention of the soil causing further softening of the material. Observed moisture contents varied from 20% to 25% for lime-treated soils and from 18% to 23% for cement-treated soils. Higher moisture contents recorded in lime-treated soils are consistent with the low shear modulus values recorded.

Initial and final small strain shear modulus values were calculated to assess the reductions in shear modulus over time in chemically treated sulfate bearing soils. Shear modulus variation with time was also calculated. The specific results of the shear modulus measurements made on the treated soil samples using the bender element are discussed next.

As a reference for comparison, typical small strain shear modulus values for treated soils are presented in Table 16.

TABLE 16

Typical Small Strain Shear Modulus Values for Soils

| | $G_{max}$ (MPa) | |
|---|---|---|
| Soil Type | Min. | Max. |
| Soft Clays | 3 | 14 |
| Firm Clays | 7 | 35 |
| Silty Sands | 28 | 138 |
| Dense Sands and Gravel | 69 | 346 |

Shear modulus enhancements were observed for both cement-treated and lime-treated natural (not spiked) Riverside soils. The lowest initial shear modulus was recorded for 4% lime-treated soil (27.2 MPa) and the highest shear modulus value was recorded at 6% cement dosage (58.9

MPa). Final shear modulus values were 50% higher than the initial shear modulus values in both cement-treated and lime-treated soil. Maximum enhancements to shear modulus were obtained in the Riverside soil, as the original sulfate level of this soil is too low (500 ppm) to cause deleterious ettringite formation reactions.

For the other soils (spiked Burleson, Okla., spiked Riverside), both lime and cement treatments showed reduced shear moduli over elapsed time periods. For 4% lime treated soils, the initial shear modulus varied from 26.5 MPa to 27.3 MPa. For the 8% lime-treated soils, the initial shear modulus varied from 17.2 MPa to 28.8 MPa. It was observed that in lime-treated soils, the increase in stabilizer dosage had minimal impact on the shear moduli values. In Oklahoma soil, the shear modulus at 4% lime dosage was 27.4 MPa, while the shear modulus at 8% lime dosage was 17.2 MPa.

For 3% cement-treated soils, the initial shear moduli values varied from 18.78 MPa to 31.17 MPa and for 6% cement-treated soils, the initial shear moduli varied from 34.93 MPa to 57.6 MPa. For cement-treated soils, shear modulus increased with an increase in dosage levels in general.

Overall, it can be seen that shear moduli values were higher for cement-treated soils than for lime-treated soils. Though higher shear modulus values were observed with increased stabilizer dosages, loss in shear modulus was the highest for cement treatment when compared to lime treatment of the same materials.

Also, the shear modulus values for different treatments were plotted over the elapsed time periods, and the slopes of the change in modulus over time (time rates of change of modulus) were determined. The slope or time rate of change is expressed in MPa/Hr. The changes (generally, decreases) in stiffness were calculated from the slopes of the lines, for different soils, stabilizers, and stabilizer dosages. Thus, the slopes of the line reflect the variation in shear modulus (stiffness) over time; a positive slope indicates a gain in stiffness over time and a negative slope indicates a loss in stiffness over time. The determined initial and final shear modulus and stiffness loss (MPa/Hr.) for the different soils and treatments are presented in Tables 17-21 below.

Table 17 presents the results from the natural Riverside soil which, due to its low sulfate level (500 ppm sulfate), is an outlier here, showing an increase in stiffness (the slope of the line is positive indicating a gain in strength). The following discussion of Tables 18-21 refers to the soils other than the natural Riverside soil.

From Tables 18 through 21, it can be observed that in 4% lime-treated soils, the stiffness loss is calculated as 0.005 MPa/Hr; whereas for 8% lime-treated soils, this value is around 0.010 MPa/Hr. From stiffness loss values, one can note that at higher lime dosages, the sulfate reactions occur at a faster pace, leading to material softening and consequently reduction in small strain shear moduli. In cement-treated soils, the stiffness loss varied from 0.013 MPa/Hr. to 0.063 MPa/Hr at 3% and 6% cement treatments, respectively. The increase in stiffness loss at higher cement dosages is indicative of the destabilizing reactions in cement-treated sulfate-bearing soils. The observed stiffness losses are in line with the volumetric swell values observed in the soils under study.

Among the three soils considered in the current study, the Burleson soil is a fat CH clay type and the soils from Oklahoma and Riverside are CL lean clays. The observed stiffness loss is higher in some of the tests for the fat clayey soil when compared with the lean clayey soils. The high plasticity nature of the Burleson soil and sulfate contents in excess of 10,000 ppm could be the reasons for larger moduli reduction rates than in low plasticity soils.

Overall, the loss of stiffness is greater in the cement-treated soils as compared to the lime-treated soils. The stiffness loss in the cement-treated soils is 3 to 4 times higher than that in the lime-treated soils.

TABLE 17

Rate of Change of Stiffness in MPa/Hr. for Lime & Cement Treated Riverside Soil

| | Riverside Soil (Sulfate Content: 500 ppm) | | | |
|---|---|---|---|---|
| Soil | Initial | Final | Gain | Stiffness Rate (MPa/Hr.) |
| 4% Lime | 27.2 | 36.44 | 9.2 | 0.043* |
| 8% Lime | 29.1 | 44.7 | 15.6 | 0.072 |
| 3% Cement | 31.35 | 47.8 | 16.45 | 0.076 |
| 6% Cement | 58.9 | 76.8 | 17.9 | 0.083 |

*Positive Sign Indicates Strength Improvements

TABLE 18

Rate of Change of Stiffness in MPa/Hr. for 4% Lime Treatment

| | 4% Lime | | | | |
|---|---|---|---|---|---|
| Soil | Initial | Final | Loss | Stiffness Rate (MPa/Hr.) | Volumetric Swell (%) |
| Burleson | 26.52 | 24.86 | 1.66 | −0.008* | 17.2 |
| Oklahoma | 27.36 | 26.69 | 0.67 | −0.003 | 10.8 |
| Riverside | 26.59 | 25.9 | 0.69 | −0.003 | 14.8 |

*Negative Sign Indicates Strength Losses

TABLE 19

Rate of Change of Stiffness in MPa/Hr. for 8% Lime Treatment

| | 8% Lime | | | | |
|---|---|---|---|---|---|
| Soil | Initial | Final | Loss | Stiffness Rate (MPa/Hr.) | Volumetric Swell (%) |
| Burleson | 27.01 | 26.79 | 0.22 | −0.001* | 15.6 |
| Oklahoma | 17.23 | 14.46 | 2.77 | −0.013 | 14.6 |
| Riverside | 28.86 | 25.15 | 3.71 | −0.017 | 16 |

*Negative Sign Indicates Strength Losses

TABLE 20

Rate of Change of Stiffness in MPa/Hr. for 3% Cement Treatment

| | 3% Cement | | | | |
|---|---|---|---|---|---|
| Soil | Initial | Final | Loss | Stiffness Rate (MPa/Hr.) | Volumetric Swell (%) |
| Burleson | 30.85 | 28.15 | 2.7 | −0.013* | 12.8 |
| Oklahoma | 18.78 | 15.76 | 3.02 | −0.014 | 11.2 |
| Riverside | 31.17 | 27.14 | 4.03 | −0.019 | 13.8 |

*Negative Sign Indicates Strength Losses

TABLE 21

Rate of Change of Stiffness in MPa/Hr.
for 6% Cement Treated Soils

| Soil | 6% Cement | | | | |
| --- | --- | --- | --- | --- | --- |
| | Initial | Final | Loss | Stiffness Rate (MPa/Hr.) | Volumetric Swell (%) |
| Burleson | 41.91 | 28.26 | 13.65 | −0.063* | 16.1 |
| Oklahoma | 34.93 | 27.22 | 7.71 | −0.036 | 14.3 |
| Riverside | 57.6 | 52.35 | 5.25 | −0.024 | 15.2 |

*Negative Sign Indicates Strength Losses

The above examples of data collected are not intended to be limiting or exhaustive. Additional types of data may be collected as will be understood by those of ordinary skill in the art in view of the present disclosure. For example, data correlating magnitude of swell with change in moisture over time may be obtained.

The data collected also includes the soil constants a and b (as well as associated data, e.g., data necessary to determine the soil constants a and b) for each specific soil (e.g., type, properties, and conditions) to be field tested. As described below in the discussion of time domain reflectometry (TDR), these soil-specific constants a and b are used in calculating the moisture content of the soil from the apparent dielectric constant of the soil, which is obtained from the TDR measurements.

With the appropriate data in hand, field testing can be conducted. Field testing may be conducted by testing a small test area of a site on which it is planned to build a structure (e.g., road, building, etc.). Based on the results of the testing performed on the test area, the expected heave and associated risks for construction, of the site as a whole, may be determined. With this method of testing, the testing of the test area may be conducted in a relatively short time period, and it is not necessary to subject the site as a whole to the stringent requirements of testing (e.g., treatment with stabilizers, hydration, curing, etc.). Accordingly, a great reduction of labor, resources, time and money may be realized. The testing described herein may also be referred to as methods rather than tests. The methods may be referred to as methods of indirectly assessing soil heave. In the following, the methods are described initially, followed by a description of systems and apparatuses which may be used in carrying out the methods. Due to the nature of the subject matter, some aspects of the methods are described more fully in the latter section describing the systems and apparatuses.

FIG. 1 illustrates a flow chart depicting a method that may be used to assess soil heave, according to some embodiments. (For convenience, both the flow chart and the method depicted thereby may be referred to herein by reference numeral 100.) Method 100 may be performed on soil of a test area of a site of interest, e.g., a site at which it is desired or planned to construct a structure on the soil. At step 102, data may be collected pertaining to the particular soil type, properties and conditions at the site of interest. The data may include data correlating any of moisture content, dry density, and shear modulus with soil swell, for the particular soil type, properties and conditions at the site of interest. The data may also include the soil-specific constants a and b. The data may also include other properties pertaining to the particular soil/conditions at the site of interest. The collection of this data is further described elsewhere in this disclosure. The data collection step may have been performed well in advance of the more direct field testing carried out in subsequent steps.

At step 105, a sample of the soil may be taken from the (test area of the) site, and properties of the soil of the sample may be determined, e.g., in a laboratory. Such properties may include, without limitation, e.g., one or more Atterberg limits, sulfate content, Unified Soil Classification System (USCS) classification, optimal moisture content, maximum dry density, pH, etc. Such properties may be obtained by methods known to those of ordinary skill in the art, as discussed elsewhere herein. At step 110, the soil at the test area of the site may be treated with a stabilizer, i.e., a stabilizer may be added to the soil. The stabilizer may be a calcium-based stabilizer, such as lime, cement, or fly ash. The dosage of the stabilizer added to the soil may be determined based on the determined soil properties, e.g., dry density. At step 115, properties of the stabilizer-treated soil may be determined, e.g., a Proctor compaction test may be performed to determine the optimal moisture content and maximum dry density. The dosage of stabilizer to be added to the soil may be determined by an iterative process in which soil properties are determined multiple times before and after stabilizer treatment (or modification of treatment, e.g., change of dosage). At step 120, the treated soil may be compacted to a targeted density, e.g., based on a Proctor curve of the treated soil. At step 123, the treated soil may be allowed to cure for a period of time, e.g., 72 hours, to gain strength.

At step 125, a bender element (BE) and a time domain reflectometer (TDR) probe may be inserted into the soil in the test area. In order to accomplish the insertion, a hole may be dug in the soil. As described in greater detail with reference to FIG. 7 below, the TDR probe may be placed vertically in the hole, the hole may be partly refilled with soil, the BE may be placed horizontally in the soil at a depth intermediate between the end of the TDR probe (located at the bottom of the hole) and the head of the TDR probe (located at the top of the hole), and the remainder of the hole may be refilled with soil. The filled hole may be recompacted.

At step 130, the soil in the hole (or the entire test area) may be hydrated, that is, moisture (water) may be added to the soil. Step 130 may be repeated multiple times over a period of time in order to keep the soil hydrated, e.g., to a desired (minimum) degree or extent. The degree or extent of hydration may be set based on a result a Proctor compaction test of the soil. At step 135, the shear modulus of the soil in the hole may be determined. As described in greater detail below, this determination may be made by determining the shear velocity based on the output signal of the BE, and calculating the shear modulus using a formula relating the shear modulus to the shear velocity. Step 135 may be repeated multiple times over a period of time in order to determine a change in shear modulus of the soil over time. Step 135, or a portion thereof, may also be characterized as including the following: providing a plurality of determined values of a shear modulus of soil, the determined values being values of the shear modulus of the soil at different times; and determining a change over time in the shear modulus of the soil, based on the plurality of determined values of the shear modulus of the soil. At step 140, the moisture content of the soil in the hole may be determined. As described in greater detail below, this determination may be made by determining the apparent dielectric constant of the soil based on the output signal of the TDR probe, and calculating the moisture content using a formula relating the moisture content to the apparent dielectric constant. Step 140 may be repeated multiple times over a period of time in order to determine a change in moisture content of the soil over time. The period of time over which steps 130, 135 and 140 may be repeated may be approximately one week. Alternatively, this period of time may be shorter or longer than one week, e.g., a matter of days, weeks or months.

According to some embodiments, method 100 may be carried out performing both steps 135 and 140, while according to some embodiments method 100 may be carried out performing only one of 135 and 140.

Although steps 130, 135 and 140 are shown as successive steps in flow chart 100, steps 130, 135 and 140 may be carried out concurrently over the same period of time. As mentioned, each of steps 130, 135 and 140 may be repeated multiple times over the period of time. Accordingly, the statement that steps 130, 135 and 140 may be performed "concurrently" is to be understood as admitting of a wide range of possibilities. For example, it is possible but not necessary that given iterations of these respective steps be carried out simultaneously, e.g., that a given iteration of step 135 be carried out simultaneously with a given iteration of step 140. It is also possible that the set of all iterations of any one of the three steps, say, 135, be carried out over the same time period as the set of all iterations of any other of the three steps, say, 140. It is also possible that the time period during which the set of all iterations of any one of the three steps, say, 135, is carried out overlaps the time period during which the set of all iterations of another of the three steps, say, 140, is carried out. The above examples are not intended to be limiting or exhaustive, and any permutations are possible. Of course, it is also not necessary that steps 130, 135 and 140 be carried out concurrently.

In place of or in addition to steps 135 and/or 140, the dry density of the soil in the hole may be determined. This determination may be made based on the output signal of the TDR probe, and it may be repeated multiple times over a period of time (e.g., the same period of time during which steps 130, 135 and/or 140 are performed) in order to determine a change in dry density of the soil over time.

At step 145, the magnitude of swell (if any) of the soil in the hydrated test area may be estimated. This estimate may be based on the determined change over time in the shear modulus of the soil (determined in step 135), the determined change over time in the moisture content of the soil (determined in step 140), and/or (although not indicated in flow chart 100) the determined change over time in the dry density of the soil (discussed above as an alternative or addition to steps 135 and 140). This estimate may be made using the previously obtained correlations between swell and (change over time of) shear modulus, moisture content and/or dry density, for the particular soil type, properties and conditions. The swell whose magnitude is estimated may be any or all of the volumetric swell, the vertical swell and the horizontal swell.

Step 145 may be performed at the end of the period of time during which steps 130, 135 and 140 are performed. Alternatively or in addition, step 145 may be performed after the end of that period of time, and/or before the end of that period of time.

At step 150, the heave of the soil in the hydrated test area may be assessed. Specifically, for example, the magnitude of the heave may be estimated, and the time required for occurrence of heave (which may be referred to herein as "timeframe of heave"), e.g., of a given magnitude, may be estimated. The magnitude and timeframe of heave are correlated with the swell of the soil, especially the volumetric and vertical swell, but may also be influenced by other factors such as soil type and certain soil properties and conditions. These factors may be taken account of in arriving at the estimates of the magnitude and timeframe of heave. Volumetric or vertical swell may be used as a stand-in for heave, it being understood that these quantities may not be exactly directly correlated with heave and that other factors may also play a role in heave. Having estimated the heave that occurred on the soil in the hydrated test area, the heave expected to occur on the soil of the entire site may be estimated. The site would be expected to undergo the same heave as occurred on the sample, except for certain effects such as those due to (1) differences between future (e.g., environmental) conditions of the site and the past conditions (e.g., hydration, etc.) under which the soil in the test area was evaluated, (2) different constraints on heave in the soil of the site versus the soil of the sample (e.g., in the soil of the site, horizontal heave is generally constrained by the adjacent soil, while the soil of the sample is not surrounded by adjacent soil), and (3) differences between properties of the soil of the site and properties of the soil of the sample. These differences may be taken account of using the collected data, other data, and theoretical knowledge, so that these effects may be estimated. In this way, the heave potential of an entire site may be estimated with a high degree of accuracy based on testing that may be completed, in many cases, in a period of time on the order of magnitude of one week. This time period is sufficiently short to make this testing feasible to perform on planned construction sites, without interfering with or constraining the construction schedule.

At step 155, the relative predominance in the soil of either sulfate reactions (resulting in the formation of ettringite) or pozzolanic reactions may be determined. This determination may be made based on the previously obtained correlation data and on the estimated heave. For example, an estimated magnitude of heave above a certain threshold may indicate the predominance of the sulfate reactions, while an estimated magnitude of heave below a certain threshold may indicate predominance of the pozzolanic reactions. As another example, a change in shear modulus that is zero or negative (i.e., a reduction in shear modulus) found for stabilizer-treated soil may indicate that sulfate reactions (resulting in the formation of ettringite) predominate relative to pozzolanic reactions.

At step 160, the effectiveness of the stabilizer treatment on the soil may be assessed. This assessment may be made based on the previously obtained correlation data and on the estimated heave. Also, an evaluation of the prospects for construction on the site may be made. This evaluation may include a determination of a level of risk (e.g., low, moderate, or high) of damage expected to be caused by heave to a structure that would be built on the site if the soil of the site is treated with stabilizer. Based on the level of risk, it may be decided to proceed with treating the site with stabilizer and building on the site (e.g., in the case of a low or no risk), or (in the case of a moderate or high risk) to take measures to mitigate expected heave before building on the site (e.g., additional treatment of the site, e.g., adding material to or on top of the existing soil, or removing the soil and replacing it with soil having different properties, etc.) or to transfer the planned construction to a different site. As an example, a magnitude of heave of 10% or more, or in certain circumstances, 5% or more, may support a determination that the level of risk of damage to structures expected to be caused by heave is significant, such that construction should not proceed without mitigation measures.

It will be understood that steps 150, 155 and 160 may be performed in any order relative to each other or simultaneously. (Steps 155 and 160 can be based on the results of step 145 and/or step 150.)

It will be understood that one or more steps of method 100 may be omitted depending on the circumstances and purposes of performing the method. For example, one or more of steps 110 (adding stabilizer), 120 (compacting), 123 (curing), 130 (hydrating) may be omitted. For example, method 100 may be applied to soils that have low levels of sulfates or no sulfates, and under these circumstances adding stabilizer may not be desired. One or more of steps 102, 105, and 115 may be omitted or combined with each other, for example, where soil of known type and properties is being tested. One or more of steps 135-160 may be omitted, e.g., where the information (to be determined, etc.) is already known or not needed. Step 125 may be modified where one or both of the bender element and TDR probe are not being used, either where use of one of these two elements alone suffices or where alternate methods/apparatuses for determining the desired soil properties/information are used. Step 125 may be omitted, e.g., where pertinent measurements have already been made and only determinations (such as those set forth in any of steps 135-160) based on the measurements remain to be made.

As will be understood by one of ordinary skill in the art upon reading the present disclosure, some or all of the calculations, determinations, estimations, assessments and the like included in the above-described steps may be performed by a determination module, which module may include any or all of the apparatuses or systems (e.g., bender element system, time domain reflectometry system, and computer system), or components thereof, described herein as performing these actions.

Systems and apparatuses for assessing soil heave will be described with reference to FIGS. 2-8. (References made herein to a group of numerically consecutive figures, e.g., FIGS. "2-8," are intended to refer to all the figures within the indicated numerical range, including those figures that also include a letter designation, e.g., FIGS. 4A and 4B.) Specifically, a bender element will be described with primary reference to FIG. 2, a bender element system including a bender element and associated equipment will be described with primary reference to FIG. 2, a time domain reflectometer (TDR) probe will be described with primary reference to FIGS. 4A and 4B, and a TDR system including a TDR probe and associated equipment will be described with primary reference to FIGS. 5 and 6. These systems and apparatuses may perform methods falling under the description of method 100 (it being understood that that description covered many variations and hence a plurality of methods) or further variations thereof such as will be understood by those of ordinary skill in the art upon reading this disclosure.

Bender elements are piezoelectric devices which may be used, among other things, to measure shear wave velocity in soil. A piezoelectric element or transducer is an electromechanical converter, that is, it converts electrical energy into mechanical energy and vice versa. When excited by the voltage differential of an electrical signal, the piezoelectric element flexes or bends (mechanical motion), and when forced to bend, the piezoelectric element generates a voltage differential.

A bender element includes a pair of piezoelectric transducers, one serving as a transmitter and the other serving as a receiver. An electrical signal is applied to the piezoelectric transmitter, causing it to generate a wave in the medium in which the piezoelectric element is disposed. The wave travels through the medium and impinges upon the piezoelectric receiver, causing it to bend. The bending of the receiver generates an output electric signal. The input voltage or transmitted signal and the output signal are both recorded on a timescale, so that the travel time of the wave (from transmitter to receiver) can be determined.

In the context of the present disclosure the bender element is used to determine the velocity of a shear wave through soil, from which the shear modulus can be obtained. The shear wave velocity, $V_S$, can be determined by the following equation:

$$V_S = L/t \qquad (1)$$

where L is the distance traveled by the shear wave (through the soil specimen), which equals the (e.g., tip-to-tip) distance between the piezoelectric transmitter and the piezoelectric receiver, and t is the time taken by the shear wave to travel the distance L. The shear modulus, $G_{max}$, of a medium can be calculated from the velocity of the shear wave through the medium by the following equation:

$$G_{max} = \rho V_S^2 \qquad (2)$$

where $\rho$ is the density of the medium (in this case, the soil).

The shear modulus is the ratio of shear stress to shear strain, and is also referred to as stiffness. Accordingly, a higher shear modulus indicates a stiffer material: more stress is required to achieve the same strain, or the same stress achieves less strain. The shear modulus is often represented as $G_0$ in equation (2). The term $G_{max}$ may be used to refer to the small strain shear modulus, which is the shear modulus in the small strain range, where shear strains or deformations are purely elastic and the relationship between shear stress and shear strain is generally linear. In the small strain range, the shear modulus reaches a nearly constant limiting value of the maximum shear modulus. Given the small displacements of a bender element, the shear modulus values obtained from use of this device can be defined as being in the small strain range.

Figure 2:
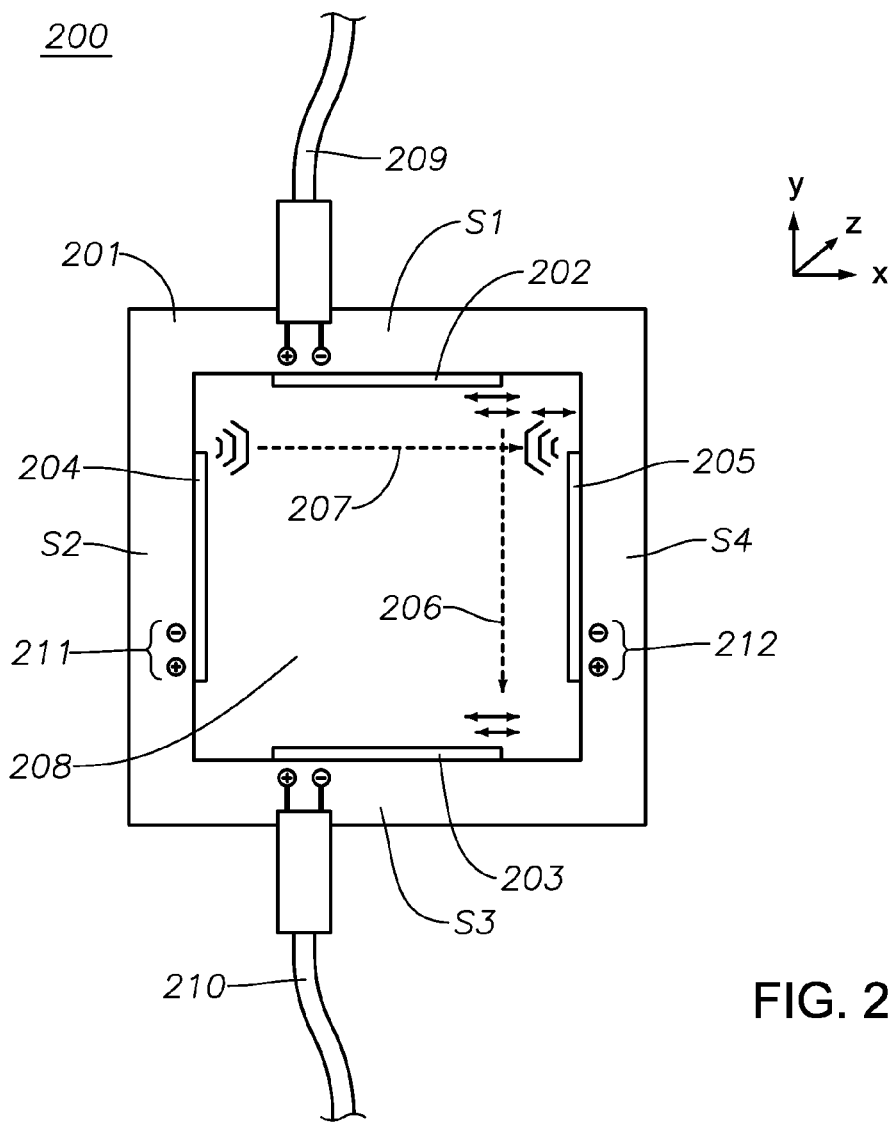
FIG. 2 is a top plan view of a bender element, according to some embodiments.

Turning to FIG. 2, a bender element 200, according to some embodiments, will be described. Bender element 200 includes a frame 201 in which piezoelectric elements 202, 203, 204, 205 are housed or mounted, supported and protected. Although not required, frame 201 advantageously may have a shape that permits a pair of piezoelectric elements (e.g. the pair 202, 203, or the pair 204, 205) to be disposed across from one another, with the soil to be tested disposed between the pair of piezoelectric elements (as will be made clear below). Such advantageous shape may be a rectangle or square, as shown in FIG. 2, or another shape.

Frame 201 may have a single pair or (as illustrated) two pairs of opposed piezoelectric elements. The use of the term "opposed" here is intended to convey that the two piezoelectric elements of the pair are respectively mounted on opposed sides of the frame 201 (in this case, frame 201 has a square shape, and the sides of frame 201 are the four sides of the square). Piezoelectric element 202 may be said to be mounted on a first side S1 of frame 201; piezoelectric element 204 may be said to be mounted on a second side S2 of frame 201, adjacent the first side S1; piezoelectric element 203 may be said to be mounted on a third side S3 of frame 201, adjacent the second side S2 and opposed to the first side S1; and piezoelectric element 205 may be said to be mounted on a fourth side S4 of frame 201, adjacent the third side S3 and the first side S1 and opposed to the second side S2. Piezoelectric elements 202, 203 (a first pair of piezoelectric elements) are opposed to each other, and piezoelectric elements 204, 205 (a second pair of piezoelectric elements) are opposed to each other.

A first pair of piezoelectric elements 202, 203 may be piezoelectric bender elements, and a second pair of piezoelectric elements 204, 205 may be piezoelectric extender elements. Piezoelectric bender elements bend upon application of an electric signal, while piezoelectric extender elements extend upon application of an electric signal. Piezoelectric bender elements 202, 203 may be used to measure shear wave velocity, while piezoelectric extender elements 204, 205 may be used to measure compression wave velocity. Upon application of an electric signal, piezoelectric bender element 202 (transmitter) generates a shear wave 206 in the direction of piezoelectric bender element 203 (receiver). Piezoelectric bender element 203 receives the shear wave 206 from piezoelectric bender element 202, causing piezoelectric bender element 203 to bend and generate an electric voltage. As discussed, the times of the input and output voltages are recorded, whereby the travel time of the shear wave 206 may be determined. As the distance traveled (distance between transmitter 202 and receiver 203) may readily be measured, the shear wave velocity may be obtained from equation (1). As the density of the medium (the soil) through which the shear wave 206 traveled is readily determinable, the shear modulus may be obtained from equation (2). The density of the medium (soil) may be determined by measuring the mass and volume thereof.

In some embodiments, piezoelectric extender elements 204 (transmitter), 205 (receiver) may be used to send and receive a compression wave 207 and measure its velocity for the purpose of obtaining additional information pertaining to soil properties.

Figure 3:
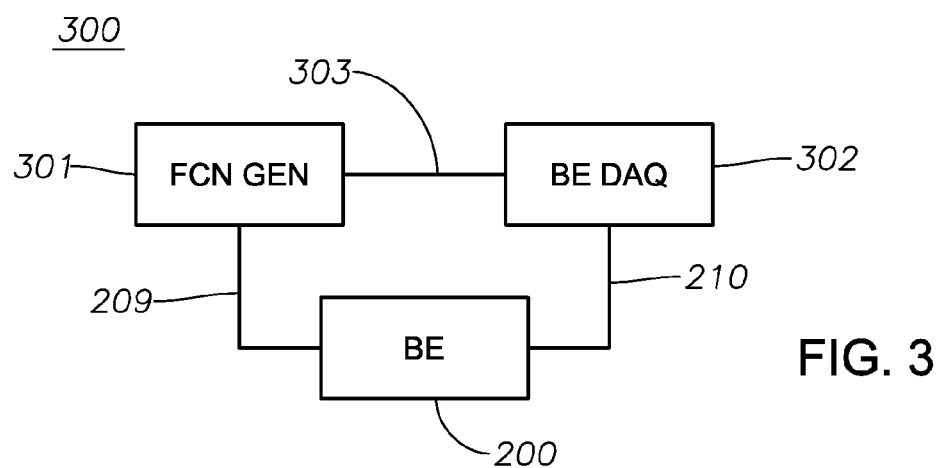
FIG. 3 is a block diagram illustrating a bender element system, according to some embodiments.

In operation, the soil under test would be present in the central region 208 of frame 201. A cable 209 would supply the input electric signal to piezoelectric bender element 202 (transmitter), and a cable 210 would receive the output electric signal from piezoelectric bender element 203 (receiver) and transmit it to a data acquisition unit, discussed below (FIG. 3). When piezoelectric extender elements 204, 205 are to be used another pair of cables (not shown) like cables 209, 210 would be connected to piezoelectric extender elements 204, 205 at the connection points 211, 212 for each of piezoelectric extender elements 204, 205. It will be understood to those of ordinary skill in the art that piezoelectric elements 202, 203 may be used interchangeably as transmitter and receiver, and piezoelectric extender elements 204, 205 may be used interchangeably as transmitter and receiver.

Piezoelectric elements 202, 203, 204, 205 may be any of various kinds, e.g., ceramic-based, polymer-based, or ceramic/polymer composite. Frame 201 may be formed of e-glass or another material, preferably one that provides a degree of strength, stiffness and durability, so as not to corrode in the soil and so as to protect and keep in place the piezoelectric elements 202, 203, 204, 205. A protective cover may be provided to prevent soil from becoming trapped in bender element 201. Bender element may also be coated with wax, covered with vinyl tape and vacuum grease, or the like, at the connections between the cables and the piezoelectric elements 202, 203, 204, 205 to prevent moisture from entering the connections. Example dimensions of bender element 200 are 2 inches in length (x direction or y direction) of frame 201, 5 mm thickness (z direction) of frame 201, and 1 inch in length of each of piezoelectric elements 202, 203 (x direction), 204, 205 (y direction). These dimensions are not to be taken as limiting. Of course, frame 201 may be thicker than piezoelectric elements 202, 203, 204, 205 in order to protect piezoelectric elements 202, 203, 204, 205. Technical arrangements necessary to achieve various conditions conducive to obtaining reliable measurements (e.g., electrical shielding and insulation, physical alignment of transmitter and receiver, good contact with soil, elimination or reduction of noise, etc.) will be known to those of ordinary skill in the art.

Turning to FIG. 3, a bender element system 300, in which bender element 200 may be used, will be described. Bender element system 300 includes a function generator or signal generator 301, a data acquisition unit (DAQ) 302 and bender element 200. According to some embodiments, function generator 301 and DAQ 302 may be provided in a single unit. DAQ 302 may include, e.g., a digital oscilloscope. Function generator 301 generates the input electric signal supplied via cable 209 to bender element 200 (transmitter 202). As noted, this input electric signal is also supplied to DAQ 302, via an electrical connection 303, so that the start of the travel time of the wave may be recorded. The output electric signal from bender element 200 (receiver 203) is conveyed to DAQ 302 via cable 210. Accordingly, both start and end travel times are recorded by DAQ 302, whereby travel time of the wave 206 may be measured, from which the shear wave velocity, and thence the shear modulus, may be obtained. By obtaining the shear modulus at different times, the change over time of the shear modulus may be calculated.

For convenience, only a simplified depiction and description of bender element system 300 is provided herein, it being understood that those of ordinary skill in the art will appreciate additional instrumentation and operations that may be advantageously employed in such a system. For example, in practice, bender element system 300 may include signal amplifier(s), filter, voltage divider, etc. One of ordinary skill in the art will also know the appropriate operating parameters for use in bender element system 300, such as type and frequency of electric signals applied to bender element 200. The electric signals applied to the bender element 200 may be any of various kinds, e.g., sine wave, square wave, triangular wave, etc. Various signal frequencies may be used; the resonant frequency of the bender element 200 or the bender element-soil system may be used. In addition, various methods of determining travel time from the output signal may be used, e.g., first time of arrival, first peak-to-peak time, cross correlation. According to some embodiments, the second inversion of the output signal may be used, as the first inversion may be masked by noise or by a compression wave signal. Stacking of multiple successive output waves may be performed.

In time domain reflectometry (TDR), a signal is sent down a wire or other conductor and one or more reflections of the signal are received and analyzed. In the case of TDR used for soil measurements, the conductor may be referred to as a TDR probe or waveguide. The so-called apparent length (described below) of the signal between two points on the TDR probe (reflecting the speed or travel time of the signal between those two points) is obtained from the received reflections of the input signal, and is used to determine the apparent dielectric constant of the soil (described below). From the apparent dielectric constant, properties of the soil, such as the moisture content and dry density, may be obtained. Further details as to how soil properties are obtained from TDR measurements are given below (see FIG. 6).

Figures 4A, 4B:
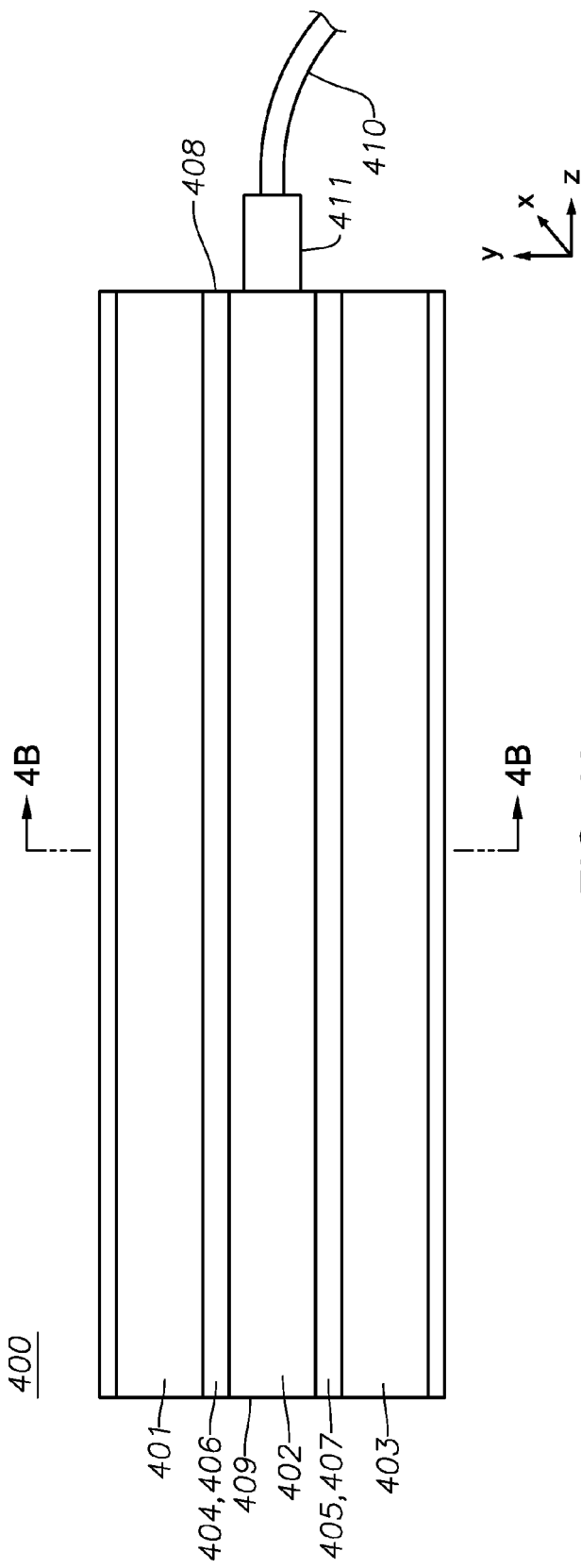
FIG. 4A is a plan view of a time domain reflectometer (TDR) probe, according to some embodiments.
FIG. 4B is a cross-sectional view, taken along the line 4B-4B in FIG. 4A, of a time domain reflectometer (TDR) probe, according to some embodiments.

Turning to FIGS. 4A and 4B, a time domain reflectometer (TDR) probe, according to some embodiments, will be described. A TDR probe may also be referred to as a waveguide. A TDR probe 400 includes one or more prongs, e.g., two prongs, three prongs (as shown) or another number of prongs. Each of the prongs 401, 402, 403 may be formed as a substantially flat metal strip, though other configurations are possible. Prongs 401, 402, 403 may be aligned in parallel along their longitudinal axis (z axis) as shown. Between each pair of adjacent prongs, there is a gap: between prongs 401, 402 there is a gap 404, and between prongs 402, 403 there is a gap 405. Each of gaps 404, 405 is filled with a respective filler: gap 404 is filled with filler 406, and gap 405 is filled with filler 407. Fillers 406, 407 may be silicon tape or another material. Fillers 406, 407 may occupy the entire space of the gaps 404, 405, respectively, and may serve to eliminate air gaps between the prongs 401, 402, 403. Air gaps could cause erroneous measurements, e.g., of moisture content.

One longitudinal end 408 of TDR probe 400 is referred to as the "head of the probe" and the other longitudinal end 409 of TDR probe 400 is referred to as the "end of the probe." A cable 410 from a pulse generator (discussed below, FIG. 5) is connected to TDR probe 400 at head 408 thereof. TDR probe 400 may be provided with a connection head 411, at head 408, for connecting cable 410 to probe 400. A signal from the pulse generator is inputted into TDR probe 400 via cable 410 at head 408 of probe 400, and the signal travels along the length (z axis) of probe 400 from head 408 to end 409 of probe 400. As will be discussed below (FIG. 7), in field testing of soil, head 408 will be the top of probe 400 and will be disposed at the top of the soil (at ground level) and end 409 will be the bottom of probe 400 and will be disposed in the soil (underground).

Turning to FIG. 4B specifically, prongs 401, 402, 403 may be coated with a protective coating 412, to protect them from deleterious effects caused by environmental factors, e.g., corrosion. Protective coating 412 may be a polymer tape or another material. Protective coating 412 may be coated on any or all sides A, B, C, D shown in FIG. 4B.

Example dimensions of TDR probe 400 may be: each of prongs 401, 402, 403 may be between 8 and 20 mm in length (distance in the z direction), e.g., about 12.7 mm; each gap 404, 405 may be 2 to 4 mm in width (distance in the y direction), e.g., 3 mm. These dimensions are not to be taken as limiting.

Figure 5:
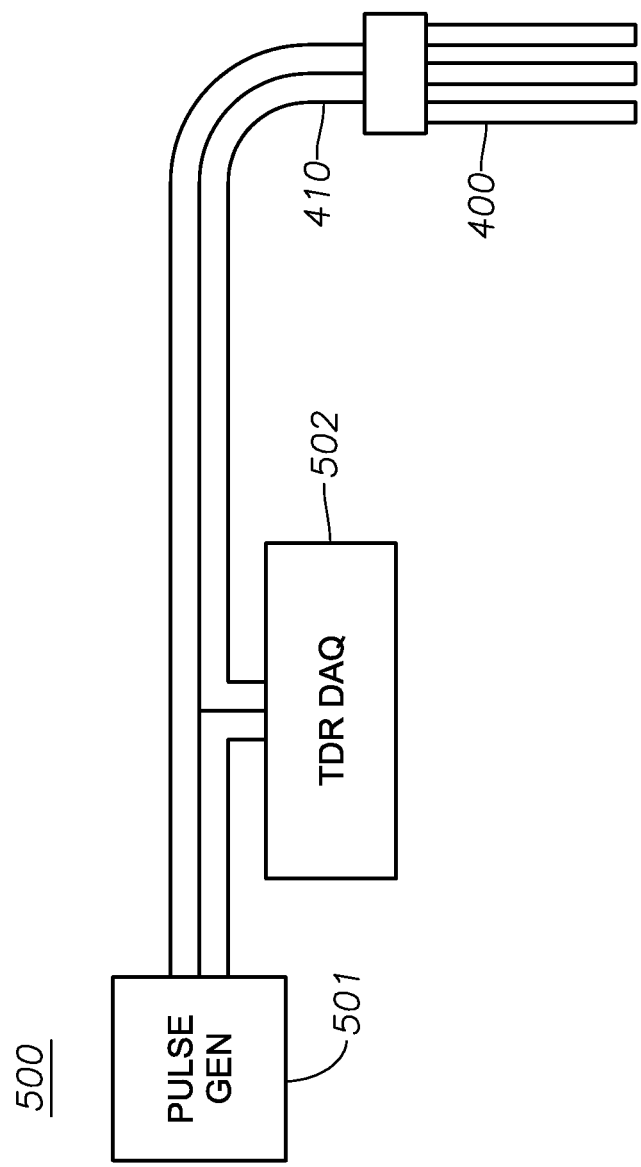
FIG. 5 is a schematic illustration of a TDR system, according to some embodiments.

Turning to FIG. 5, a TDR system 500, in which TDR probe 400 may be used, will be described. TDR system 500 includes a pulse generator 501, a data acquisition unit (DAQ) 502 and TDR probe 400. According to some embodiments, pulse generator 501 and DAQ 502 may be provided in a single unit. DAQ 502 may include, e.g., a sampling receiver and a display or recording device. Pulse generator 501 generates an input signal, which is supplied via cable 410 to TDR probe 400. This input signal may also be supplied to DAQ 502. Reflections of the inputted signal received from TDR probe 400 are conveyed to DAQ 502 via cable 410. As noted above and described further below, reflections from the start (head) and end of the probe 400 are recorded by DAQ 502, whereby travel time of the signal along the probe 400 may be measured, from which measurement the moisture content of the soil may ultimately be obtained. By obtaining the moisture content at different times, the change over time of the moisture content may be calculated.

For convenience, only a simplified depiction and description of TDR system 500 is provided herein, it being understood that those of ordinary skill in the art will appreciate additional instrumentation and operations that may be advantageously employed in such a system. One of ordinary skill in the art will also know the appropriate operating parameters for use in TDR system 500.

Figure 6:
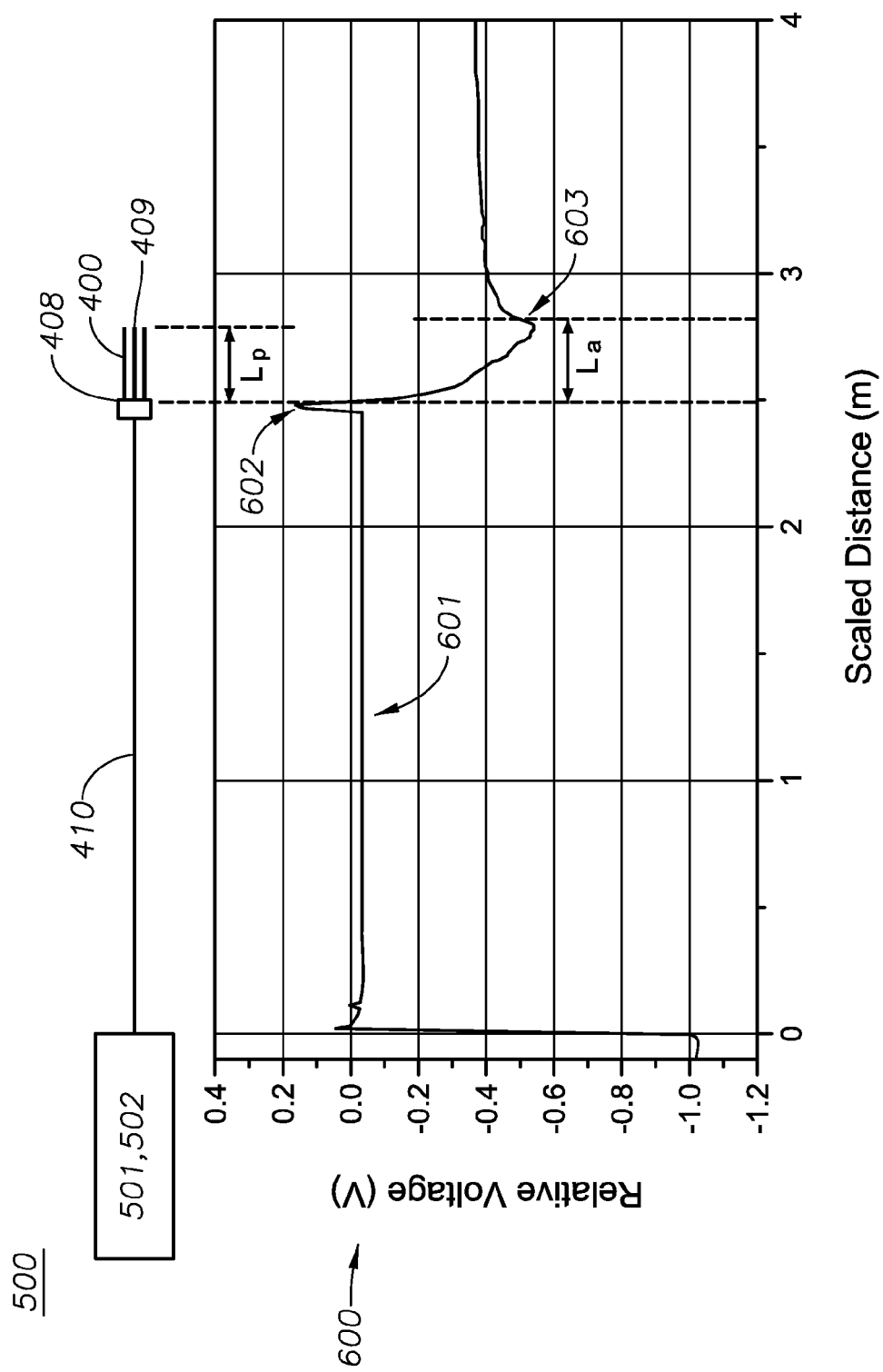
FIG. 6 shows a schematic illustration of a TDR system aligned with an illustration of a waveform (reflected signals) from the TDR system, showing the correspondence between travel of the signal in the TDR system and travel of the signal as represented by the waveform, according to some embodiments.

Turning to FIG. 6, analysis of the TDR output signal (reflections of the input signal) and determination of soil properties based thereon, according to some embodiments, will be described. FIG. 6 shows a schematic illustration of TDR system 500 aligned with an illustration of a waveform 601 (reflected signals) from the TDR system 500, showing the correspondence between the travel of a signal in the TDR system 500 and the travel of the signal as represented by the waveform 601, according to some embodiments. Waveform 601 is shown on a Cartesian coordinate system 600 whose y axis is relative voltage (V) and whose x axis is scaled distance (m). The x axis may also be understood to indicate time. In FIG. 6, pulse generator 501 and TDR DAQ 502 are shown as combined in a single unit.

As the input signal from the pulse generator 501 travels from the pulse generator 501 along cable 410 to TDR probe 400, the voltage on graph 600 reads as zero, as there is not yet any reflection of that signal (the cable is assumed not to have defects or faults). When the input signal reaches head 408 of TDR probe 400 (which is a point of discontinuity), a reflection 602 of the signal is generated and conveyed back to DAQ 502. This reflection 602 from probe head 408, which may be referred to as the first reflection, appears on the graph 600 as a distinct change in voltage. When the input signal reaches end 409 of TDR probe 400 (which is another point of discontinuity), another reflection 603 of the signal is generated and conveyed back to DAQ 502. This reflection 603 from probe end 409, which may be referred to as the second reflection, appears on the graph 600 as a distinct change in voltage. The distance on the graph 600 between the first reflection 602 and the second reflection 603 is referred to as the apparent length ($L_a$), i.e., the apparent length of TDR probe 400 (from probe head 408 to probe end 409) on the graph 600. The apparent length reflects the time it took the input signal to travel the length of TDR probe 400 or the travel speed at which the input signal traveled along the length of TDR probe 400. In these senses, the apparent length corresponds to the actual physical length ($L_p$) of TDR probe 400.

In practice, $L_a$ may be determined by obtaining and plotting the first derivative of all the points in the waveform 600. Then, the method of tangents may be used to analyze the waveform 600 and the first derivative of all the points to obtain the apparent length $L_a$. For the sake of simplicity, further details of these procedures are omitted, as they are known to those of ordinary skill in the art.

As $L_a$ and $L_p$ can thus be determined, the apparent dielectric constant ($K_a$) of the soil may be determined from equation (3):

$$K_a = \left(\frac{L_p}{L_a}\right)^2 \tag{3}$$

Once the apparent dielectric constant is known, the moisture content of the soil may be determined from equation (4):

$$\sqrt{K_a}\frac{\rho_w}{\rho_d} = a + bw \tag{4}$$

where $\rho_w$ is the density of water, $\rho_d$ is the dry density of the soil, a and b are calibration constants specific to the given soil, and w is the gravimetric water content, i.e., the moisture content, of the soil. The gravimetric water content is the ratio of the mass of the water to the mass of the dry soil solids. In contrast, the volumetric water content is the volume of water as a percentage of the total volume of the soil.

Accordingly, in order to determine the moisture content, the constants a and b must be obtained for the specific soil under test. Thus, as noted above, these constants are part of the data that is collected in advance for each specific soil (e.g., type, properties and conditions) to be field tested.

The soil-specific constants a and b for a given soil may be obtained as follows. In brief, a series of tests may be performed using successive samples of the soil, e.g., in a compaction mold, the successive samples having different water contents. Then the total density, apparent dielectric constant and water contents for each sample are determined. Oven drying may be used. Then $$\sqrt{K_a}\frac{\rho_w}{\rho_d}$$

versus ω is plotted from the series of tests, and a straight line is fitted to the data. Soil constant a is obtained as the zero-intercept (y-intercept) of the line and soil constant b is obtained as the slope of the line (it being seen that equation (4) is of the form y=mx+c, where m is the slope and c is the y-intercept).

A more detailed version of the procedure for obtaining soil-specific constants a and b is given below. According to this procedure, the following steps are performed.
1) Determine the volume of the mold and the mass of the empty mold.
2) Obtain soil samples from the representative testing site.
3) Air-dry the required amount of soil sample that will be used for calibration testing, using the oven.
4) Use the air-dried sample to prepare three soil specimens for different moisture contents (20%, 25% and 30%). (The moisture contents are selected such a way as to simulate the expected range of moisture contents observed in the field.)
5) Place the soil in the mold to a certain height and compact it, using an aluminum rod. Place the TDR probe on top of the soil and fill the rest of the mold with the soil specimen. (Proper care should be taken while compacting the soil along the TDR probe so that no damage is caused to the probe.)
6) Weigh the mold along with the wet soil. (Since the weight of the empty mold and the volume of the mold are known, the density of the soil can be calculated.)
7) Test the prepared soil specimens in the mold to obtain TDR waves using the pulse generator. Campbell Scientific software may be used to monitor the generated wave form.
8) Once the TDR waveforms are generated, collect the soil sample from each specimen to measure the gravimetric water content of the soil in accordance with ASTM D 2216.

After performing the required tests, the gravimetric water content of the soil and apparent dielectric constant values are calculated, along with the density of the soil, which are tabulated in Table 22 below. Soil-specific constants a and b are calculated by performing a series of linear regression plots. As mentioned above, soil constants a and b are found by plotting $$\sqrt{K_a}\frac{\rho_w}{\rho_d}$$

versus ω (gravimetric), where ω is the gravimetric water content, $\rho_w$ is the density of water, $\rho_d$ is the dry density of soil, and $K_a$ is the apparent dielectric constant of the soil. A best-fit line is obtained from the data where a is the zero-intercept (y-intercept) of the line and b is the slope of the line.

TABLE 22

Data Measured for Individual Soil Specimens

| Soil Specimen | Target Moisture Content (%) | Dry Density of the Soil, $\rho_d$ (kg/m³) | Apparent Dielectric Constant, Ka | TDR Parameter, $\sqrt{K_a}\frac{\rho_w}{\rho_d}$ | Gravimetric Water Content, ω |
|---|---|---|---|---|---|
| 1 | 20 | 1438.79 | 6.70 | 1.80 | 0.17 |
| 2 | 25 | 1428.23 | 11.98 | 2.42 | 0.23 |
| 3 | 30 | 1483.97 | 19.67 | 2.99 | 0.28 |

The obtaining of soil-specific constants a and b may be referred to as calibration of the TDR.

Figure 7:
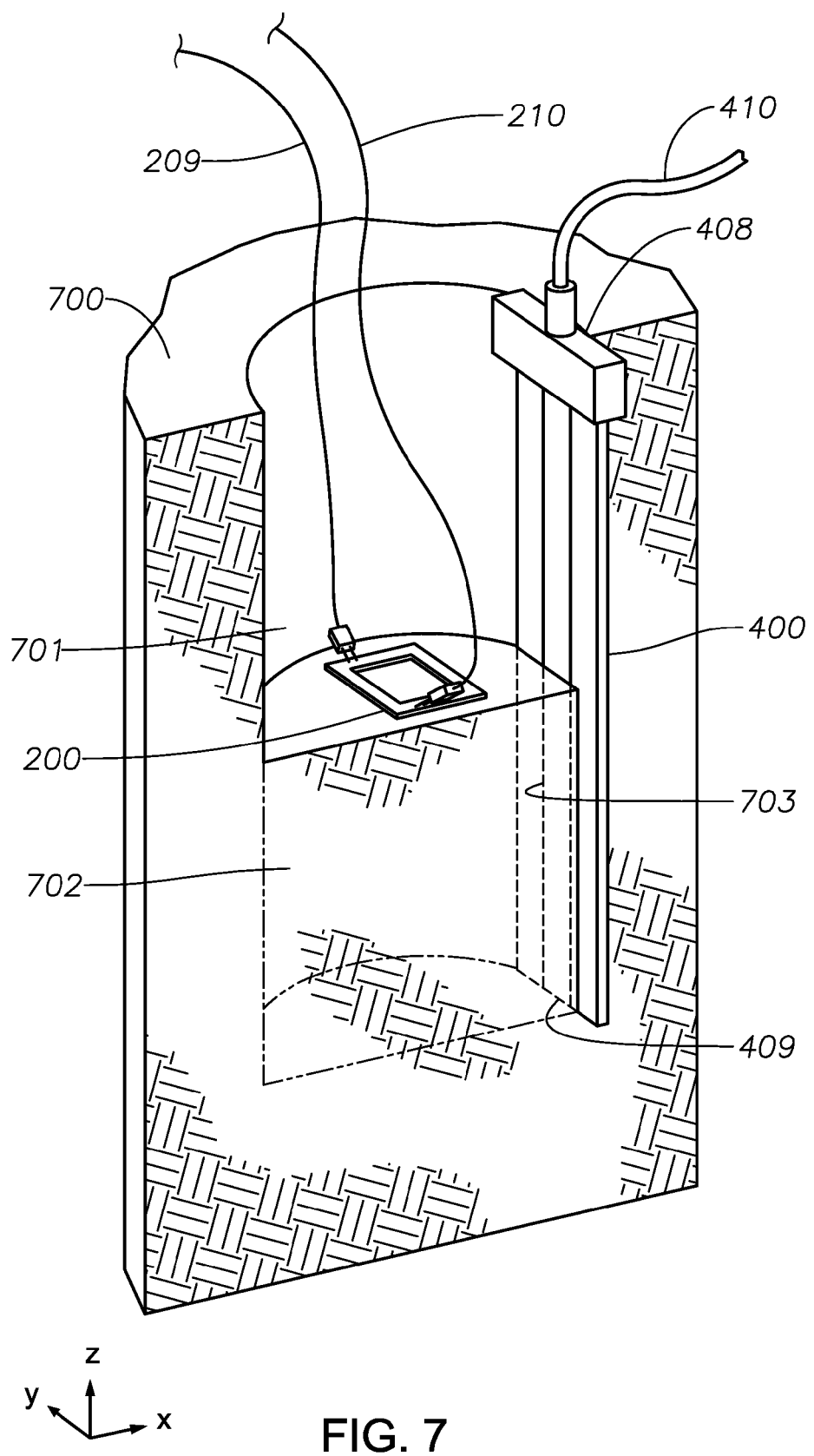
FIG. 7 is a perspective view of a bender element and a TDR probe placed in soil (in a hole in the ground) for field testing of the soil, according to some embodiments.

Turning to FIG. 7, step 125 of method 100 (see FIG. 1) will be described in further detail, according to some embodiments. In step 125, a bender element 200 and a TDR probe 400 are inserted into the soil 700 in the test area. In order to accomplish the insertion, a hole 701 may be dug in the soil 700. When the hole 701 is dug, the TDR probe 400 may be placed vertically in hole 701. Then, hole 701 may be partly refilled with soil, as shown by refilled bottom portion 702 of hole 701. Accordingly, the bottom portion 703 of TDR probe is now buried under the soil, as indicated by being shown in dashed lines. Then, the bender element 200 is placed horizontally on top of the refilled soil 702 in hole 701. Accordingly, bender element 200 is disposed at a depth intermediate between end 409 of TDR probe 400 (located at the bottom of hole 701) and head 408 of TDR probe 400 (located at the top of hole 701, even with ground level), for example, at or near mid-height of TDR probe 400, which may also be deemed mid-height (or mid-depth) of the soil sample under test. It is also possible to dispose bender element 200 at a different depth of the soil sample. Then, the remainder of hole 701 may be refilled with soil (not shown). The filled hole 701 may be recompacted. By placing bender element 200 and TDR probe 400 in these respective orientations good contact with the soil under test may be achieved. Also, these orientations provide for ease of installation and help prevent disturbing the soil under test. In the illustrated orientation, bender element generates and measures horizontal shear waves in the soil. It is also possible to employ multiple (e.g., horizontally oriented) bender elements 200 at different depths in a sample of soil under test.

FIG. 7 also illustrates cables 209, 210 connecting bender element 200 to bender element system 300 (FIG. 3), and cable 410 connecting TDR probe 400 to TDR system 500 (FIG. 5), which cables have been described above.

In alternative embodiments, bender element 200 and TDR probe 400 may be placed in the soil in different relative locations and/or orientations than those shown in FIG. 7. For example, TDR probe 400 may be placed horizontally or at an angle, and bender element 200 may be placed vertically or at an angle. If placed vertically, bender element 200 would generate and measure vertical shear waves in the soil.

It will be understood that determining shear modulus, moisture content and dry density of soil may be carried out by any appropriate methods known to those of ordinary skill in the art, and not only by the above-described bender element and TDR methods.

Figure 8:
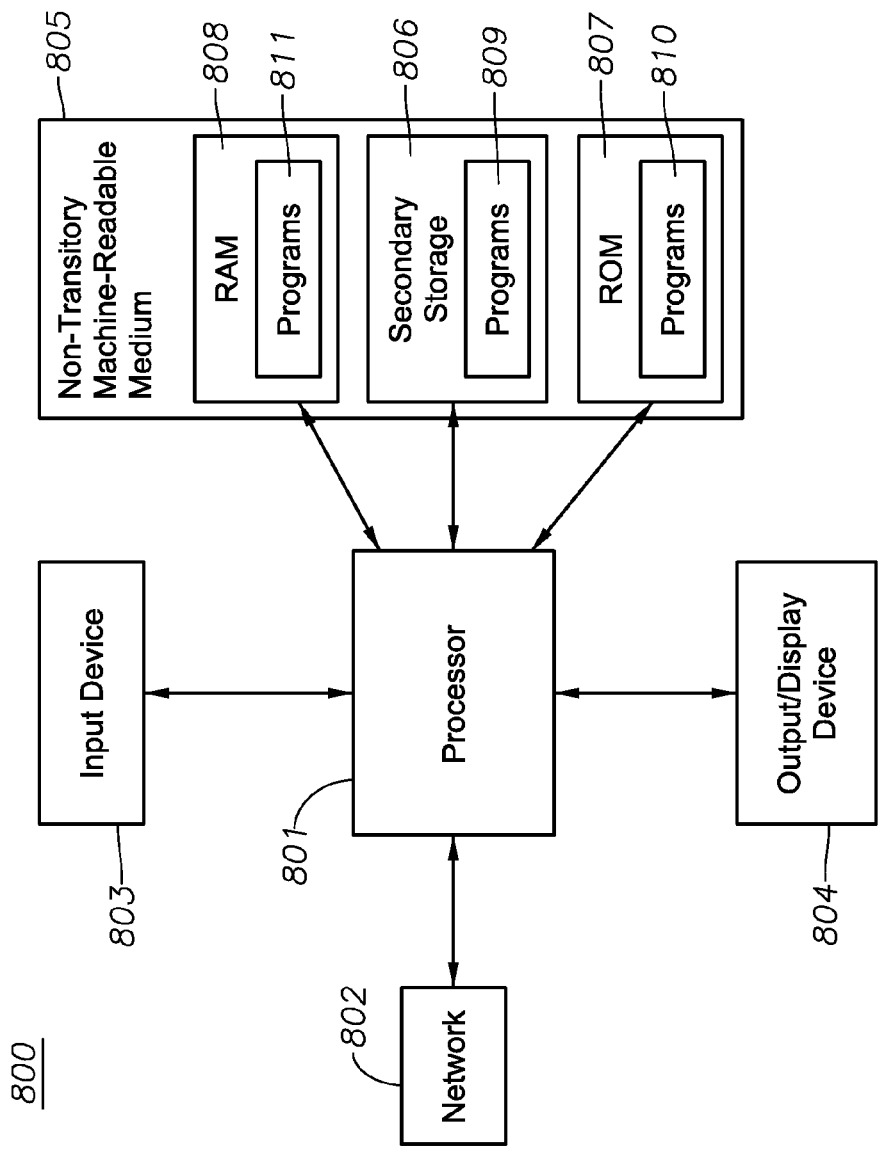
FIG. 8 is a block diagram of an exemplary computer system useful for implementing one or more embodiments.

FIG. 8 illustrates an exemplary computer system useful for carrying out functionality of one or more embodiments described herein. Such a computer system may be used with the bender element (BE) system 300 and/or TDR system 500 described herein. Such a computer system may be part of the BE system 300 and/or TDR system 500 described herein or may be operated in conjunction therewith. Such a computer system may be used, inter alia, for storing data and for performing calculations, determinations, estimations, assessments and the like, described herein.

As seen in FIG. 8, computer system 800 includes at least one processor 801, which may be a programmable control device that may be programmed to perform steps or processes described herein. Such a processor 801 may be referred to as a central processing unit (CPU) and may be implemented as one or more CPU and/or GPU (Graphics Processing Unit) chips. Processor 801 may be in communication with the BE system 300 and the TDR system 500 (not explicitly shown in FIG. 8), with a communications network 802 via network connectivity (or network interface) devices (not explicitly shown in FIG. 8), with input devices 803, with output/display devices 804, and with a non-transitory machine-readable medium 805, which may be a non-transitory computer-readable medium.

The network connectivity or network interface devices may include modems, modem banks, Ethernet cards, universal serial bus (USB) cards, serial interfaces, token ring cards, fiber distributed data interface (FDDI) cards, wireless local area network (WLAN) cards, radio transceiver cards such as code division multiple access (CDMA) and/or global system for mobile communications (GSM) radio transceiver cards, or other network devices. These network connectivity/interface devices may enable the processor 801 to communicate with the Internet or one or more intranets or other communication networks 802. With such a network connection, the processor 801 may transmit information to and receive information from other entities (including the BE system 300 and the TDR system 500), via the network 802, in the course of performing steps or processes disclosed herein.

The input devices 803 may include touch screens, keyboards, keypads, switches, dials, mice, microphones, voice recognition devices, card readers, tape readers, or other input devices.

The output/display devices 804 may include printers, monitors, displays, speakers, speech synthesizers, or other output or display devices.

The machine-readable medium 805 may comprise memory devices including secondary storage 806, read only memory (ROM) 807, and random access memory (RAM) 808. The secondary storage 806 may include any form of optical or magnetic storage including solid-state storage, such as magnetic disks (fixed, floppy, and removable) and tape; optical media such as CD-ROMs and digital video disks (DVDs); and semiconductor memory devices such as Electrically Programmable Read-Only Memory (EPROM), Electrically Erasable Programmable Read-Only Memory (EEPROM), Programmable Gate Arrays and flash devices. The secondary storage 806 may be used for non-volatile storage of data and may be used as an over-flow data storage device if the RAM 808 is not large enough to hold all working data. The secondary storage 806 may be used to store instructions or programs 809 that are loaded into the RAM 808 when such instructions or programs 809 are selected for execution. Execution of such instructions and programs 809 cause the processor 801 to perform any of the steps or processes described in this disclosure. The ROM 807 may also be used to store instructions or programs 810 and may be used to store data to be read by the processor 801 during program execution. The ROM 807 is a non-volatile memory device which typically has a small memory capacity relative to the larger memory capacity of the secondary storage 806. The RAM 808 is used to store volatile data and may also be used to store programs or instructions 811. Access to both the ROM 807 and the RAM 808 is typically faster than to the secondary storage 806.

The processor 801 executes codes, computer programs, and scripts that it accesses from secondary storage 806, the ROM 807, the RAM 808, or the network connectivity/interface devices. The terms "logic" and "module" as referred to herein relate to structure for performing one or more logical operations. For example, a module may comprise circuitry which provides one or more output signals based upon one or more input signals. Such circuitry may comprise a finite state machine that receives a digital input and provides a digital output, or circuitry which provides one or more analog output signals in response to one or more analog input signals. Such circuitry may be provided in an application specific integrated circuit (ASIC) or field programmable gate array (FPGA). Also, a module may comprise machine-readable instructions stored in a memory in combination with processing circuitry to execute such machine-readable instructions. However, these are merely examples of structures which may provide logic, and embodiments disclosed herein are not limited in this respect. Also, items such as applications, modules, components, etc. may be implemented as software constructs stored in a machine-readable storage medium, and those constructs may take the form of applications, programs, subroutines, instructions, objects, methods, classes, or any other suitable form of control logic. Steps or processes described herein may thus be performed by software, hardware, firmware, or any combination of one or more of these.

The computer system 800 may include a server and one or more separate user interface devices (not explicitly shown), which may be client devices. As suggested by the server-client configuration, the system may be used to interface with a number of users or entities (e.g., BE systems and TDR systems), e.g., to process data (e.g., perform calculations, determinations, estimations, assessments or the like) for multiple test sites.

The communication network(s) 802 may include any one or more of a wired network, a wireless network (e.g., Wi-Fi network or cellular network), and facilities for data transmittal over telecommunications networks and services, and the network interface may include appropriate corresponding interfaces. Communication over the communication network(s) 802 may occur in real-time when network connectivity is available. Alternatively, or when network connectivity is not available for immediate transmission, the data for transmission over the network 802 may be stored locally in memory/storage and transmitted at a later time.

Memory/storage (e.g., secondary storage 806) may also include one or more databases, which may be used to store, e.g., data pertaining to soil types, properties and conditions; data pertaining to soil constants a and b or data associated with such data; correlation data; and/or generated output data.

According to some embodiments, a user interface device may be implemented using the computer system 800, which may be modified as appropriate for a user interface (e.g., mobile) device. However, as noted, one or more user interfaces may also be implemented by one or more separate computer devices.

Such user interface device may be a mobile (e.g., client) device or a web (e.g., client) device. Mobile devices are electronic devices that are portable or mobile and include, e.g., mobile phones, such as smartphones (e.g., iPhones™, Android™ phones, Windows™ phones, BlackBerry™ smartphones), tablets (e.g., iPads™, Android™, Microsoft Surface™ tablets), etc. Web devices are electronic devices that are not considered (as) portable or mobile as mobile devices and include, e.g., personal computers, such as laptop and desktop computers, etc. The user interface device may but need not be remote from other elements described in this disclosure.

After reading the description presented herein, it will become apparent to a person skilled in the relevant arts how to implement embodiments disclosed herein using computer systems/architectures and communication networks other than those described herein.

In light of the principles and example embodiments described and illustrated herein, it will be recognized that the example embodiments can be modified in arrangement and detail without departing from such principles. Also, the foregoing discussion has focused on particular embodiments, but other configurations are also contemplated. In particular, even though expressions such as "in one embodiment," "in another embodiment," or the like are used herein, these phrases are meant to generally reference embodiment possibilities, and are not intended to limit the invention to particular embodiment configurations. As used herein, these terms may reference the same or different embodiments that are combinable into other embodiments. As a rule, any embodiment referenced herein is freely combinable with any one or more of the other embodiments referenced herein, and any number of features of different embodiments are combinable with one another, unless indicated otherwise or so dictated by the description herein.

Similarly, although example methods or processes have been described with regard to particular steps or operations performed in a particular sequence, numerous modifications could be applied to those methods or processes to derive numerous alternative embodiments of the present invention. For example, alternative embodiments may include methods or processes that use fewer than all of the disclosed steps or operations, methods or processes that use additional steps or operations, and methods or processes in which the individual steps or operations disclosed herein are combined, subdivided, rearranged, or otherwise altered. Similarly, this disclosure describes one or more embodiments wherein various operations are performed by certain systems, applications, module, components, etc. In alternative embodiments, however, those operations could be performed by different components. Also, items such as applications, module, components, etc. may be implemented as software constructs stored in a machine accessible storage medium, such as an optical disk, a hard disk drive, etc., and those constructs may take the form of applications, programs, subroutines, instructions, objects, methods, classes, or any other suitable form of control logic; such items may also be implemented as firmware or hardware, or as any combination of software, firmware and hardware, or any combination of any two of software, firmware and hardware. The term "processor" may refer to one or more processors.

Further, each of the method embodiments set forth above, including all combinations of method embodiments, may also be instantiated as an article of manufacture embodiment, wherein an article of manufacture comprises a non-transitory machine-accessible medium containing instructions, the instructions comprising a software application or software service, wherein the instructions, when executed by the machine, cause the machine to perform the respective method. The machine may be, e.g., a processor, a processor-based system such as the systems described herein, or a processor-based device such as the user interface device described herein.

This disclosure may include descriptions of various benefits and advantages that may be provided by various embodiments. One, some, all, or different benefits or advantages may be provided by different embodiments.

In view of the wide variety of useful permutations that may be readily derived from the example embodiments described herein, this detailed description is intended to be illustrative only, and should not be taken as limiting the scope of the invention. What is claimed as the invention, therefore, are all implementations that come within the scope of the following claims, and all equivalents to such implementations.

What is claimed is:

1. A method comprising:
   using a bender element, disposed on or in soil, providing a plurality of determined values of a shear modulus of the soil, the determined values being values of the shear modulus of the soil, at a given depth of the soil, at different times;
   determining a change over time in the shear modulus of the soil, based on the plurality of determined values of the shear modulus of the soil;
   determining a change over time in moisture content of the soil, comprising determining the moisture content of the soil at successive times using a time domain reflectometer (TDR) probe disposed at least partly in the soil, the TDR probe comprising one or more prongs; and
   estimating a magnitude of swell of the soil based on the determined change over time in the shear modulus of the soil, the determined change over time in the moisture content of the soil, and correlations between change in shear modulus, change in moisture content and swell, determined for a type of the soil.

2. The method of claim 1:
   wherein the soil has been treated by adding a stabilizer to the soil, and
   wherein the soil is hydrated.

3. The method of claim 2, wherein the stabilizer is lime or cement.

4. The method of claim 2, wherein the hydrating of the soil is to an extent based on a result of a Proctor compaction test of the soil.

5. The method of claim 2, wherein the stabilizer has been added to the soil in a dosage based on a dry density of the soil.

6. The method of claim 1, wherein the providing a plurality of determined values of a shear modulus of the soil, the determined values being values of the shear modulus of the soil, at a given depth of the soil, at different times, comprises determining respective values of the shear modulus of the soil at successive times.

7. The method of claim 1, wherein the bender element is located at substantially mid-height of a sample of the soil under test, wherein the bender element is oriented horizontally in the soil, and wherein the bender element is disposed surrounding the sample of the soil under test.

8. The method of claim 1, wherein the TDR probe is oriented vertically in the soil.

9. The method of claim 1, further comprising any one or more of the following: estimating a magnitude and/or timeframe of heave of the soil; assessing an effectiveness of a stabilizer in stabilizing the soil, the stabilizer having been added to the soil; determining a relative predominance of sulfate reactions resulting in formation of ettringite or pozzolanic reactions in the soil; and assessing a risk of heave-induced damage to a structure that would be constructed on the soil.

10. A system comprising:
- a bender element disposed on or in soil, for determining a change over time of a shear modulus of the soil; and
- a time domain reflectometer (TDR) probe disposed at least partly in the soil and comprising one or more prongs, the TDR probe for determining a change over time of moisture content of the soil,
- wherein the determined change over time of the shear modulus, the determined change over time of the moisture content, and correlations between change in shear modulus, change in moisture content and swell, are used to assess heaving of the soil,
- wherein the bender element is used to provide a plurality of determined values of the shear modulus of the soil, at a given depth of the soil, at different times, and
- wherein the TDR probe is used to determine the moisture content of the soil at successive times.

11. A system according to claim 10, further comprising a determination module for (A) determining at least one of (i) the shear modulus of the soil based on output from the bender element and (ii) the moisture content of the soil based on output from the TDR probe, and (B) estimating heaving of the soil based on at least one of (i) the change over time of the shear modulus and (ii) the change over time of the moisture content.

12. A system according to claim 10, wherein the bender element comprises a plurality of piezoelectric elements arranged on a frame, including two piezoelectric elements arranged opposite each other on the frame.

13. A system according to claim 12,
- wherein the frame comprises a substantially rectangular-shaped frame comprising a first side, a second side adjacent the first side, a third side adjacent the second side and opposed to the first side, and a fourth side adjacent the third side and the first side and opposed to the second side, and
- wherein the plurality of piezoelectric elements comprises a piezoelectric bender element on the first side, a piezoelectric bender element on the third side, a piezoelectric extender element on the second side and a piezoelectric extender element on the fourth side.

14. A system according to claim 10, wherein the TDR probe comprises a plurality of parallel prongs.

15. A system according to claim 14,
- wherein the plurality of parallel prongs comprises three flat metal strips aligned in parallel with a gap between any two adjacent strips, and
- wherein each of the gaps is filled with a filler.

16. An article of manufacture comprising a non-transitory machine-readable medium comprising instructions that, when executed, cause a machine to:
- determine a change over time in a shear modulus of the soil, based on a plurality of determined values of the shear modulus of the soil, the determined values being values of the shear modulus of the soil, at a given depth of the soil, at different times;
- determine a change over time in moisture content of the soil, based on a plurality of determined values of the moisture content of the soil, the determined values being values of the moisture content of the soil at successive times; and
- estimate a magnitude of swell of the soil based on the determined change over time in the shear modulus of the soil, the determined change over time in the moisture content of the soil, and correlations between change in shear modulus, change in moisture content and swell, determined for a type of the soil,
- wherein a bender element disposed on or in the soil is used to determine the plurality of determined values of the shear modulus of the soil, and
- wherein a time domain reflectometer (TDR) probe disposed at least partly in the soil and comprising one or more prongs is used to determine the plurality of determined values of the moisture content of the soil.

* * * * *